(12) United States Patent
Quay et al.

(10) Patent No.: US 7,244,709 B2
(45) Date of Patent: Jul. 17, 2007

(54) COMPOSITIONS AND METHODS FOR ENHANCED MUCOSAL DELIVERY OF PARATHYROID HORMONE

(75) Inventors: Steven C. Quay, Edmonds, WA (US); Henry R. Costantino, Woodinville, WA (US); Mary S. Kleppe, Kingston, WA (US); Ching-Yuan Li, Bellevue, WA (US)

(73) Assignee: Nastech Pharamecutical Company Inc., Bothell, WA (US)

( * ) Notice: Subject to any disclaimer, the term of this patent is extended or adjusted under 35 U.S.C. 154(b) by 0 days.

(21) Appl. No.: 11/126,996

(22) Filed: May 10, 2005

(65) Prior Publication Data
US 2005/0276843 A1    Dec. 15, 2005

Related U.S. Application Data

(60) Provisional application No. 60/570,113, filed on May 10, 2004.

(51) Int. Cl.
*A61K 38/29* (2006.01)
*A61K 31/724* (2006.01)

(52) U.S. Cl. .......................... 514/12; 424/450; 514/58
(58) Field of Classification Search ...................... None
See application file for complete search history.

(56) References Cited

U.S. PATENT DOCUMENTS

| | | | |
|---|---|---|---|
| 5,164,368 A | | 11/1992 | Recker |
| 5,578,567 A | | 11/1996 | Cardineau et al. |
| 5,952,008 A | * | 9/1999 | Backstrom et al. ......... 424/499 |
| 5,977,070 A | | 11/1999 | Piazza et al. |
| 6,416,503 B1 | | 7/2002 | Suzuki et al. |
| 6,472,505 B1 | * | 10/2002 | Condon et al. ............. 530/317 |
| 6,590,081 B1 | * | 7/2003 | Zhang ........................ 530/399 |
| 6,756,480 B2 | * | 6/2004 | Kostenuik et al. ....... 530/387.1 |
| 2003/0039654 A1 | | 2/2003 | Kostenuik et al. |
| 2004/0077540 A1 | * | 4/2004 | Quay .......................... 514/12 |
| 2005/0203002 A1 | * | 9/2005 | Tzannis et al. ................ 514/4 |
| 2005/0215475 A1 | * | 9/2005 | Ong et al. .................... 514/12 |
| 2006/0052306 A1 | | 3/2006 | Costantino et al. |
| 2006/0062758 A1 | * | 3/2006 | Cui et al. .................. 424/85.1 |

FOREIGN PATENT DOCUMENTS

| | | |
|---|---|---|
| EP | 0747054 A2 | 12/1996 |
| EP | 0878201 A2 | 11/1998 |
| JP | 5238929 A | 9/1993 |
| JP | 10130171 A | 5/1998 |
| WO | WO 2005051456 A2 | 6/2005 |
| WO | WO 2005115441 | 12/2005 |

OTHER PUBLICATIONS

Codrons, V.; Vanderbist, F.; Verbeeck, R. K.; Arras, M.; Lison, D.; Preat, V.; and Vanbever, R.; "Systemic Delivery of Parathyroid Hormone (1-34) Using Inhalation Dry Powders in Rats;" *J Pharm Sci*; May 2003; 92 (5): 938-950.

Newman, S. P.; Pitcairn, G. R.; and Dalby, R. N.; "Drug Delivery to the Nasal Cavity: in Vitro and in Vivo Assessment;" *Crit Rev. Ther Drug Carrier Syst*; 2004; 21 (1); 21-66.

* cited by examiner

*Primary Examiner*—Marianne P. Allen
*Assistant Examiner*—Cherie Woodward
(74) *Attorney, Agent, or Firm*—Peter J. Knudsen

(57) ABSTRACT

Pharmaceutical compositions and methods are described comprising at least a parathyroid hormone peptide (PTH) preferably $PTH_{1-34}$ and one or more mucosal delivery-enhancing agents for enhanced nasal mucosal delivery of PTH, for treating or preventing osteoporosis or osteopenia in a mammalian subject, preferably a human.

32 Claims, No Drawings

SEQUENCE LISTING

<160> NUMBER OF SEQ ID NOS: 3

<210> SEQ ID NO 1
<211> LENGTH: 84
<212> TYPE: PRT
<213> ORGANISM: Homo sapiens

<400> SEQUENCE: 1

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asn Val Asp Val Leu Thr Lys
65                  70                  75                  80

Ala Lys Ser Gln
```

```
<210> SEQ ID NO 2
<211> LENGTH: 34
<212> TYPE: PRT
<213> ORGANISM: Homo sapiens

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 3
<211> LENGTH: 31
<212> TYPE: PRT
<213> ORGANISM: Homo sapiens

<400> SEQUENCE: 3

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30
```

COMPOSITIONS AND METHODS FOR ENHANCED MUCOSAL DELIVERY OF PARATHYROID HORMONE

This application claims the benefit of U.S. Provisional Application No. 60/570,113, filed May 10, 2004, which is hereby incorporated by reference in its entirety.

BACKGROUND OF THE INVENTION

The teachings of all the references cited in the present specification are incorporated in their entirety by reference.

Osteoporosis can be defined as a systemic skeletal disease characterized by low bone mass, microarchitectural deterioration of bone tissue, and increased bone fragility and susceptibility to fracture. It most commonly affects older populations, primarily postmenopausal women.

The prevalence of osteoporosis poses a serious health problem. The National Osteoporosis Foundation has estimated that 44 million people are experiencing the effects of osteoporosis or osteopenia. By the year 2010, osteoporosis will affect more than 52 million people and, by 2020, more than 61 million people. The prevalence of osteoporosis is greater in Caucasians and Asians than in African-Americans, perhaps because African-Americans have a higher peak bone mass. Women are affected in greater numbers than men are because men have a higher peak bone density. Furthermore, as women age the rate of bone turnover increases, resulting in accelerated bone loss because of the lack of estrogen after menopause.

The goal of pharmacological treatment df osteoporosis is to maintain or increase bone strength, to prevent fractures throughout the patient's life, and to minimize osteoporosis-related morbidity and mortality by safely reducing the risk of fracture. The medications that have been used most commonly to treat osteoporosis include calcium, and vitamin D, estrogen (with or without progestin), bisphonates, selective estrogen receptor modulators (SERMs), and calcitonin.

Parathyroid hormone (PTH) has recently emerged as a popular osteoporosis treatment. Unlike other therapies that reduce bone resorption, PTH increases bone mass, which results in greater bone mineral density (BMD). PTH has multiple actions on bone, some direct and some indirect. PTH increases the rate of calcium release from bone into blood. The chronic effects of PTH are to increase the number of bone cells both osteoblasts and osteoclasts, and to increase the remodeling bone. These effects are apparent within hours after PTH is administered and persist for hours after PTH is withdrawn. PTH administered to osteoporotic patients leads to a net stimulation of bone formation especially in trabecular bone in the spine and hip resulting in a highly significant reduction in fractures. The bone formation is believed to occur by the stimulation of osteoblasts by PTH as osteoblasts have PTH receptors.

Parathyroid hormone (PTH) is a secreted, 84 amino acid residue polypeptide having the amino acid sequence Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe Val Ala Leu Gly Ala Pro Leu Ala Pro Arg Asp Ala Gly Ser Gln Arg Pro Arg Lys Lys Glu Asp Asn Val Leu Val Glu Ser His Glu Lys Ser Leu Gly Glu Ala Asp Lys Ala Asn Val Asp Val Leu Thr Lys Ala Lys Ser Gln (SEQ ID NO: 1). Studies in humans with certain forms of PTH have demonstrated an anabolic effect on bone, and have prompted significant interest in its use for the treatment of osteoporosis and related bone disorders.

Using the N-terminal 34 amino acids of the bovine and human hormone Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe (SEQ ID NO: 2) for example, which by all published accounts are deemed biologically equivalent to the full length hormone, it has been demonstrated in humans that parathyroid hormone enhances bone growth particularly when administered in pulsatile fashion by the subcutaneous route. A slightly different form of PTH, human PTH(1-38) has shown similar results.

PTH preparations have been reconstituted from fresh or lyophilized hormone, and incorporate various forms of carrier, excipient and vehicle. Most are prepared in water-based vehicles such as saline, or water acidified typically with acetic acid to solubilize the hormone. The majority of reported formulations also incorporate albumin as a stabilizer [see for example Reeve et al., *Br. Med. J.*, 280:6228; (1980) Reeve et al., *Lancet*, 1:1035 (1976); Reeve et al., *Calcif. Tissue Res.*, 21:469 (1976); Hodsman et al., *Bone Miner*, 9(2):137 (1990); Tsai et al., *J. Clin. Endocrinol Metab.*, 69(5):1024 (1989); Isaac et al., *Horm. Metab. Res.*, 12(9):487 (1980); Law et al., *J. Clin Invest.* 72(3): 1106 (1983); and Hulter, *J. Clin Hypertens*, 2(4):360 (1986)]. Other reported formulations have incorporated an excipient such as mannitol, which is present either with the lyophilized hormone or in the reconstitution vehicle.

$PTH_{1-34}$ also called teriparatide is currently on the market under the brand name FORTEO®, Eli Lilly, Indianapolis, Ind. for the treatment of postnenopausal women with osteoporosis who are at high risk of fracture. This drug is administered by a once daily subcutaneous injection of 20 µg in a solution containing acetate buffer, mannitol, and m-cresol in water, pH 4. However, many people are adverse to injections, and thus become non-compliant with the prescribed dosing of the PTH. Thus, there is a need to develop an intranasal formulation of a parathyroid hormone peptide that has suitable bioavailability such that therapeutic levels can be achieved in the blood to be effective to treat osteoporosis or osteopenia. FORTEO® is manufactured by recombinant DNA technology using an *Escherichia coli* strain. $PTH_{1-34}$ has a molecular weight of 4117.87 daltons. Reviews on $PTH_{1-34}$ and its clinical that have been published, including, e.g., Brixen et al, 2004; Dobnig, 2004; Eriksen and Robins, 2004; Quattrocchi and Kourlas 2004, are hereby incorporated by reference. Forsteo is currently licensed in the US (as FORTEO®,) and Europe. The safety of teriparatide has been evaluated in over 2800 patients in doses ranging from 5 to 100 µg per day in short term trials. Doses of up to 40 µg per day have been given for up to two years in long term trials. Adverse events associated with Forsteo were usually mild and generally did not require discontinuation of therapy. The most commonly reported adverse effects were dizziness, leg cramps, nausea, vomiting and headache. Mild transient hypercalcemia has been reported with Forsteo which is usually self limiting within 6 hours.

Teriparatide has been previously been administered intranasally to humans at doses of up to 500 µg per day for 7 days in one study (Suntory News Release. Suntory Establishes Large Scale Production of recombinant human $PTH_{1-34}$ and obtains promising results from Phase 1 Clinical Trials using a Nasal Formulation. February 1999. http://www.suntory-.com/news/1999-02.html accessed 15 Apr. 2004) and in another study subjects received up to 1,000 µg per day for 3 months (Matsumoto et al. Daily Nasal Spray of $hPTH_{1-34}$ for 3 Months Increases Bone Mass In Osteoporotic Subjects.

(ASBMR 2004 presentation 1171 Oct. 4, 2004, Seattle Wash.) No safety concerns were noted with this route.

Currently Forsteo is administered as a daily subcutaneous injection. It would be preferable for patient acceptability if a non-injected route of administration were available, including nasal, buccal, gastrointestinal and dermal.

DISCLOSURE OF THE INVENTION

Preferably the parathyroid hormone and the mammal is a human. In a most preferred embodiment the parathyroid hormone peptide, is $PTH_{1-34}$, also known as teriparatide. Tregear, U.S. Pat. No. 4,086,196, described human PTH analogues and claimed that the first 27 to 34 amino acids are the most effective in terms of the stimulation of adenylyl cyclase in an in vitro cell assay. Pang et al, WO93/06845, published Apr. 15, 1993, described analogues of hPTH which involve substitutions of $Arg^{25}$, $Lys^{26}$, $Lys^{27}$ with numerous amino acids, including alanine, asparagine, aspartic acid, cysteine, glutamine, glutamic acid, glycine, histidine, isoleucine, leucine, methionine, phenylalanine, proline, serine, threonine, tryptophan, tyrosine, or valine. Other PTH analogues are disclosed in the following patents, hereby incorporated by reference: U.S. Pat. No. 5,317,010; U.S. Pat. No. 4,822,609; U.S. Pat. No. 5,693,616; U.S. Pat. No. 5,589,452; U.S. Pat. No. 4,833,125; U.S. Pat. No. 5,607,915; U.S. Pat. No. 5,556,940; U.S. Pat. No. 5,382,658; U.S. Pat. No. 5,407,911; U.S. Pat. No. 6,583,114; U.S. Pat. No. 6,541,450; U.S. Pat. No. 6,376,502; U.S. Pat. No. 5,955,425; U.S. Pat. No. 6,316,410; U.S. Pat. No. 6,110,892; U.S. Pat. No. 6,051,686; U.S. Pat. No. 5,695,955; U.S. Pat. No. 4,771,124; and U.S. Pat. No. 6,376,502.

PTH operates through activation of two second messenger systems, $G_s$-protein activated adenylyl cyclase (AC) and $G_q$-protein activated phospholipase $C_\beta$. The latter results in a stimulation of membrane-bound protein kinase Cs (PKC) activity. The PKC activity has been shown to require PTH residues 29 to 32 (Jouishomme et al (1994) J. Bone Mineral Res. 9, (1179-1189). It has been established that the increase in bone growth, i.e. that effect which is useful in the treatment of osteoporosis, is coupled to the ability of the peptide sequence to increase AC activity. The native PTH sequence has been shown to have all of these activities. The hPTH-(1-34) sequence is typically shown as:

Ser Val Ser Glu Ile Gln Leu Met His Asn Leu Gly Lys His Leu Asn Ser Met Glu Arg Val Glu Trp Leu Arg Lys Lys Leu Gln Asp Val His Asn Phe (SEQ ID NO:2).

The following linear analogue, $hPTH_{1-31}NH_2$, has only AC-stimulating activity and has been shown to be fully active in the restoration of bone loss in the ovariectomized rat model [Rixon, R. H. et al., *J. Bone Miner. Res.* 9: 1179-1189 (1994)]; Whitfield et al., *Calcified Tissue Int.* 58: 81-87 (1996)]; Willick et al, U.S. Pat. No. 5,556,940, hereby incorporated by reference:

Ser Val Ser Glu Ile Gln Leu Met His Asn Leu Gly Lys His Leu Asn Ser Met Glu Arg Val Glu Trp Leu Arg Lys Lys Leu Gln Asp Val (SEQ ID NO: 3).

The above molecule, SEQ ID NO:3, and its counterpart with a $Leu_{27}$ substitution SEQ ID NO:2 may have a free carboxyl ending instead of the amide ending. Another PTH analog is $[Leu_{27}]cyclo(Glu_{22}-Lys_{26})PTH_{1-31}$.

In other embodiments of the present invention, the PTH composition is administered in droplets exiting from an actuator form a spray plume with a measured ellipsoid (ratio of length of longest to shortest axes) of 1-2, the droplets exiting from the actuator form a spray plume with a measured ellipsoid (ratio of length of longest to shortest axes) of 1-1.3, the volume median droplet size is between 10 and 1000 microns (10<Dv, 50 <1000), where the Dv, 50 is between 30 and 300 microns, the percentage of droplets having a diameter 10 microns or less is 10% or less and the percentage of droplets having a diameter 10 microns or less is 1% or less.

The present invention is also directed to an intranasal formulation of a PTH-agonist that is substantially free of proteins or polypeptides that stabilize the formulation. In particular, the preferred formulation is free of such proteins as albumin, and collagen-derived proteins such as gelatin.

In other aspects of the present invention a transmucosal PTH peptide formulation is comprised of a PTH peptide, water and a solubilizing agent having a pH of 3-6.5. In a preferred embodiment, the solubilization agent is a cyclodextrin.

In another embodiment of the present invention a transmucosal PTH peptide formulation is comprised of a PTH peptide, water, a solubilizing agent, preferably a cyclodextrin, and at least one polyol, preferably 2 polyols. In alternate embodiments the formulation may contain one or all of the following: a chelating agent, a surface-acting agent and a buffering agent.

In another embodiment of the present invention the formulation is comprised of a PTH peptide, water, chelating agent and a solubilization agent.

In another embodiment of the present invention the formulation is comprised of a PTH peptide, water and a chelating agent having a pH of 3-6.5.

In another embodiment of the present invention the formulation is comprised of a PTH peptide, water, chelating agent and at least one polyol, preferably two polyols. Additional embodiments may include one or more of the following: a surface-active agent, a solubilizing agent and a buffering agent.

In another embodiment of the present invention the formulation is comprised of a PTH peptide, water, and at least two polyols, such as lactose and sorbitol. Additional agents, which can be added to the formulation, include, but are not limited to, a solubilization agent, a chelating agent, one or more buffering agents and a surface-acting agent.

The enhancement of intranasal delivery of a PTH peptide agonist according to the methods and compositions of the invention allows for the effective pharmaceutical use of these agents to treat a variety of diseases and conditions in mammalian subjects.

The present invention fills this need by providing for a liquid or dehydrated PTH peptide formulation wherein the formulation is substantially free of a stabilizer that is a polypeptide or a protein. The liquid parathyroid hormone formulation is comprised of water, parathyroid hormone and at least one of the following additives selected from the group consisting of polyols, surface-active agents, solubilizing agents and chelating agents. The pH of the formulation is preferably 3 to about 7.0, referably 4.5 to about 6.0, most preferably about 5.0±0.3.

Another embodiment of the present invention is an aqueous PTH formulation of the present invention is comprised of water, a PTH peptide, a polyol and a surface-active agent wherein the formulation has a pH of about 3 to about 6.5, and the formulation is substantially free of a stabilizer that is a protein or polypeptide.

Another embodiment of the present invention is an aqueous PTH peptide formulation comprised of water, PTH peptide, a polyol and a solubilizing agent wherein the formulation has a pH of about 3.0 to about 6.5, and the formulation is substantially free of a stabilizer that is a protein or polypeptide.

Another embodiment of the present invention is an aqueous PTH peptide formulation comprised of water, PTH peptide, a solubilizing agent and a surface-active agent wherein the formulation has a pH of about 3.0 to about 6.5, and the formulation is substantially free of a stabilizer that is a protein or polypeptide.

Another embodiment of the invention is an aqueous PTH peptide formulation comprised of water, a PTH peptide, a solubilizing agent, a polyol and a surface-active agent wherein the formulation has a pH of about 3.0 to about 6.5, and the formulation is substantially free of a stabilizer that is a protein or polypeptide.

In another aspect of the present invention, the stable aqueous formulation is dehydrated to produce a dehydrated PTH peptide formulation comprised of PTH peptide and at least one of the following additives selected from the group consisting of polyols, surface-active agents, solubilizing agents and chelating agents, wherein said dehydrated PTH peptide formulation is substantially free of a stabilizer that is a protein or polypeptide such as albumin, collagen or collagen-derived protein such as gelatin. The dehydration can be achieved by various means such as lyophilization, spray-drying, salt-induced precipitation and drying, vacuum drying, rotary evaporation, or supercritical $CO_2$ precipitation.

In one embodiment, the dehydrated PTH peptide is comprised of PTH peptide, a polyol and a solubilizing agent, wherein the formulation is substantially free of a stabilizer that is a protein.

In another embodiment, the dehydrated PTH peptide formulation is comprised of a PTH peptide, a polyol, and a surface-active agent wherein the PTH peptide formulation is substantially free of a stabilizer that is a protein or polypeptide.

In another embodiment, the dehydrated PTH peptide formulation is comprised of a PTH peptide, a surface-active agent, and a solubilizing agent wherein the PTH peptide formulation is substantially free of a stabilizer that is a protein or polypeptide.

In another embodiment of the present invention, the dehydrated PTH peptide formulation is comprised of a PTH peptide, a polyol, a surface-active agent and a solubilizing agent wherein the PTH peptide formulation is substantially free of a stabilizer that is a protein or polypeptide.

Another aspect of the present invention is an intranasal PTH peptide formulation contain within an actuator able to produce an aerosol of said solution, wherein the spray pattern ellipticity ratio of said aerosol is between 1.00 and 1.40 when measured at a height of between 0.5 cm and 10 cm distance from the actuator tip, which has preferably an ellipticity of between 1.00 and 1.30 and produces an aerosol of between 20 and 200 microliters per actuation.

In another embodiment, the intranasal PTH peptide solution is in an actuator, which produces an aerosol of said solution, wherein the spray pattern major and minor axes of said aerosol are between 10 and 50 mm when measured at a height of between 0.5 cm and 10 cm distance from the actuator tip. In another embodiment, an aqueous solution of a PTH peptide is in a container attached an actuator so that an aerosol of the solution is produced wherein less than 10% of the droplets produced are smaller than 10 microns in size and aerosol containing the PTH peptide contains 20 and 200 microliters solution per actuation. In another embodiment, a solution of the PTH peptide is in a container attached to an actuator so that the aerosol of the solution produced upon actuation has droplets between 25 and 700 microns.

Any solubilizing agent can be used but a preferred one is selected from the group consisting of hydroxypropyl-β-cyclodextran, sulfobutylether-β-cyclodextran, methyl-β-cyclodextrin and chitosan.

Generally a polyol is selected from the group consisting of lactose, sorbitol, trehalose, sucrose, mannose and maltose and derivatives and homologs thereof.

A satisfactory surface-active agent is selected from the group consisting of L-α-phosphatidylcholine didecanoyl (DDPC), polysorbate 20 (Tween 20), polysorbate 80 (Tween 80), polyethylene glycol (PEG), cetyl alcohol, polyvinylpyrolidone (PVP), polyvinyl alcohol (PVA), lanolin alcohol, and sorbitan monooleate.

In a preferred formulation, the PTH peptide formulation is also comprised of a chelating agent such as ethylene diamine tetraacetic acid (EDTA) or ethylene glycol tetraacetic acid (EGTA). Also a preservative such as chlorobutanol, methyl paraben, propyl paraben, butyl paraben, benzalkonium chloride, benzethonium chloride, sodium benzoate, sorbic acid, phenol, or ortho-, meta- or paracresol.

The pH is generally regulated using a buffer such as sodium citrate and citric acid, and sodium acetate and acetic acid. An alternative buffer would be acetic acid and sodium acetate or succinic acid and sodium hydroxide.

The present invention also comprehends a formulation wherein the concentration of the PTH peptide is 0.1-15.0 mg/mL, preferably 1.0-2 mg/mL and the pH of the aqueous solution is 3.0-6.5 preferably about 5.0±0.3.

The present invention further includes PTH peptide formulation wherein the concentration of the polyol is between about 0.1% and 10% (w/v) and additionally wherein the concentration of the polyol is in the range from about 0.1% to about 3% (w/v).

The instant invention also includes a formulation, wherein the concentration of the surface-active agent is between about 0.00001% and about 5% (w/v), and wherein the concentration of the surface-active agent is between about 0.0002% and about 0.1% (w/v).

The instant invention also includes a formulation, wherein the concentration of the solubilzation agent is 1%-10% (w/v), and wherein the concentration of the solubilizing agent is 2% to 5% (w/v).

The finished solution can be filtered and freeze-dried, lyophilized, using methods well known to one of ordinary skill in the art, and by following the instructions of the manufacturer of the lyophilizing equipment. This produces a dehydrated PTH peptide formulation substantially free of a stabilizer that is a protein.

In another embodiment of the present invention, a PTH peptide formulation is comprised of an PTH peptide and a pharmaceutically acceptable carrier wherein the PTH-bind peptide formulation has at least 1%, preferably 3% and most preferably at least 6% higher permeation in an in vitro tissue permeation assay than a control formulation consisting of water, sodium chloride, a buffer and the PTH peptide, as determined by the transepithelial electrical resistance assay shown in Examples 2 and 7. In a preferred embodiment, the PTH formulation is further comprised of at least one excipient selected from the group consisting of a surface-active agent, a solubilization agent, a polyol, and a chelating agent.

In exemplary embodiments, the enhanced delivery methods and compositions of the present invention provide for therapeutically effective mucosal delivery of the PTH peptide agonist for prevention or treatment of osteoporosis or osteopenia in mammalian subjects. In one aspect of the invention, pharmaceutical formulations suitable for intranasal administration are provided that comprise a therapeutically effective amount of a PTH peptide and one or more intranasal delivery-enhancing agents as described herein, which formulations are effective in a nasal mucosal delivery method of the invention to prevent the onset or progression of osteoporosis or osteopenia in a mammalian subject. Nasal mucosal delivery of a therapeutically effective amount of a PTH peptide agonist and one or more intranasal delivery-enhancing agents yields elevated therapeutic levels of the PTH peptide agonist in the subject and promotes the increase in bone mass in an individual.

The enhanced delivery methods and compositions of the present invention provide for therapeutically effective mucosal delivery of a PTH peptide for prevention or treatment of osteoporosis or osteopenia in mammalian subjects. PTH peptide can be administered via a variety of mucosal routes, for example by contacting the PTH peptide to a nasal mucosal epithelium, a bronchial or pulmonary mucosal epithelium, the oral buccal surface or the oral and small intestinal mucosal surface. In exemplary embodiments, the methods and compositions are directed to or formulated for intranasal delivery (e.g., nasal mucosal delivery or intranasal mucosal delivery).

In one aspect of the invention, pharmaceutical formulations suitable for intranasal administration are provided that comprise a therapeutically effective amount of a PTH peptide agonist and one or more intranasal delivery-enhancing agents as described herein, which formulations are effective in a nasal mucosal delivery method of the invention to prevent or treat osteoporosis.

In another aspect of the invention, pharmaceutical formulations and methods are directed to administration of a PTH peptide agonist in combination with calcium, vitamin D, bisphosphonates, calcitonin or a bone morphogenic protein. See U.S. Pat. No. 5,616,560 and U.S. Pat. No. 5,700,774, hereby incorporated by reference.

The foregoing mucosal PTH peptide formulations and preparative and delivery methods of the invention provide improved mucosal delivery of a PTH peptide to mammalian subjects. These compositions and methods can involve combinatorial formulation or coordinate administration of one or more PTH peptides with one or more mucosal delivery-enhancing agents. Among the mucosal delivery-enhancing agents to be selected from to achieve these formulations and methods are (A) solubilization agents; (B) charge modifying agents; (C) pH control agents; (D) degradative enzyme inhibitors; (E) mucolytic or mucus clearing agents; (F) ciliostatic agents; (G) membrane penetration-enhancing agents (e.g., (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule (viii) a small hydrophobic penetration enhancer; (ix) sodium or a salicylic acid derivative; (x) a glycerol ester of acetoacetic acid (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)-(xviii)); (H) modulatory agents of epithelial junction physiology, such as nitric oxide (NO) stimulators, chitosan, and chitosan derivatives; (I) vasodilator agents; (J) selective transport-enhancing agents; (K) stabilizing delivery vehicles, carriers, supports or complex-forming species with which the PTH peptide (s) is/are effectively combined, associated, contained, encapsulated or bound to stabilize the active agent for enhanced mucosal delivery; and (L) alcohols such as ethanol.

In various embodiments of the invention, a PTH peptide is combined with one, two, three, four or more of the mucosal delivery-enhancing agents recited in (A)-(K), above. These mucosal delivery-enhancing agents may be admixed, alone or together, with the PTH peptide, or otherwise combined therewith in a pharmaceutically acceptable formulation or delivery vehicle. Formulation of a PTH peptide with one or more of the mucosal delivery-enhancing agents according to the teachings herein (optionally including any combination of two or more mucosal delivery-enhancing agents selected from (A)-(K) above) provides for increased bioavailability of the PTH peptide following delivery thereof to a mucosal surface of a mammalian subject.

Thus, the present invention is a method for treating osteoporosis or osteopenia in a mammal comprising transmucosally administering a formulation comprised of a PTH peptide, such that when at 50 μg of the PTH is administered transmucosally to the mammal the concentration of the PTH peptide in the plasma of the mammal increases by at least 5 pmol, preferably at least 10 pmol per liter of plasma.

Intranasal delivery-enhancing agents are employed which enhance delivery of PTH into or across a nasal mucosal surface. For passively absorbed drugs, the relative contribution of paracellular and transcellular pathways to drug transport depends upon the pKa, partition coefficient, molecular radius and charge of the drug, the pH of the luminal environment in which the drug is delivered, and the area of the absorbing surface. The intranasal delivery-enhancing agent of the present invention may be a pH control agent. The pH of the pharmaceutical formulation of the present invention is a factor affecting absorption of PTH via paracellular and transcellular pathways to drug transport. In one embodiment, the pharmaceutical formulation of the present invention is pH adjusted to between about pH 3.0 to 6.5. In a further embodiment, the pharmaceutical formulation of the present invention is pH adjusted to between about pH 3.0 to 5.0. In a further embodiment, the pharmaceutical formulation of the present invention is pH adjusted to between about pH 4.0 to 5.0. Generally, the pH is 5.0±0.3.

As noted above, the present invention provides improved methods and compositions for mucosal delivery of PTH peptide to mammalian subjects for treatment or prevention of osteoporosis or osteopenia. Examples of appropriate mammalian subjects for treatment and prophylaxis according to the methods of the invention include, but are not restricted to, humans and non-human primates, livestock species, such as horses, cattle, sheep, and goats, and research and domestic species, including dogs, cats, mice, rats, guinea pigs, and rabbits.

In order to provide better understanding of the present invention, the following definitions are provided:

According to the present invention a parathyroid hormone peptide also includes the free bases, acid addition salts or metal salts, such as potassium or sodium salts of the peptides, and parathyroid hormone peptides that have been modified by such processes as amidation, glycosylation, acylation, sulfation, phosphorylation, acetylation, cyclization and other well known covalent modification methods.

Osteopenia is a decreased calcification or density of bone, a descriptive term applicable to all skeletal systems in which the condition is noted.

"Mucosal delivery enhancing agents" are defined as chemicals and other excipients that, when added to a formulation comprising water, salts and/or common buffers and PTH peptide (the control formulation) produce a formulation that produces a significant increase in transport of PTH peptide across a mucosa as measured by the maximum blood, serum, or cerebral spinal fluid concentration ($C_{max}$) or by the area under the curve, AUC, in a plot of concentration versus time. A mucosa includes the nasal, oral, intestional, buccal, bronchopulmonary, vaginal, and rectal mucosal surfaces and in fact includes all mucus-secreting membranes lining all body cavities or passages that communicate with the exterior. Mucosal delivery enhancing agents are sometimes called carriers.

"Non-infused administration" means any method of delivery that does not involve an injection directly into an artery or vein, a method which forces or drives (typically a fluid) into something and especially to introduce into a body part by means of a needle, syringe or other invasive method. Non-infused administration includes subcutaneous injection, intramuscular injection, intraparitoneal injection and the non-injection methods of delivery to a mucosa.

As noted above, the instant invention provides improved and useful methods and compositions for nasal mucosal delivery of a PTH peptide to prevent and treat osteoporosis or osteopenia in mammalian subjects. As used herein, prevention and treatment of osteoporosis or osteopenia means prevention of the onset or lowering the incidence or severity of clinical osteoporosis by reducing increasing bone mass, decreasing bone resporption or reducing the incidence of fractured bones in a patient.

The PTH peptide can also be administered in conjunction with other therapeutic agents such as bisphonates, calcium, vitamin D, estrogen or estrogen-receptor binding compounds, selective estrogen receptor modulators (SERMs), bone morphogenic proteins or calcitonin.

Improved methods and compositions for mucosal administration of PTH peptide to mammalian subjects optimize PTH peptide dosing schedules. The present invention provides mucosal delivery of PTH peptide formulated with one or more mucosal delivery-enhancing agents wherein PTH peptide dosage release is substantially normalized and/or sustained for an effective delivery period of PTH peptide release ranges from approximately 0.1 to 2.0 hours; 0.4 to 1.5 hours; 0.7 to 1.5 hours; or 0.8 to 1.0 hours; following mucosal administration. The sustained release of PTH peptide achieved may be facilitated by repeated administration of exogenous PTH peptide utilizing methods and compositions of the present invention.

Improved compositions and methods for mucosal administration of PTH peptide to mammalian subjects optimize PTH peptide dosing schedules. The present invention provides improved mucosal (e.g., nasal) delivery of a formulation comprising PTH peptide in combination with one or more mucosal delivery-enhancing agents and an optional sustained release-enhancing agent or agents. Mucosal delivery-enhancing agents of the present invention yield an effective increase in delivery, e.g., an increase in the maximal plasma concentration ($C_{max}$) to enhance the therapeutic activity of mucosally-administered PTH peptide. A second factor affecting therapeutic activity of PTH peptide in the blood plasma and CNS is residence time (RT). Sustained release-enhancing agents, in combination with intranasal delivery-enhancing agents, increase $C_{max}$ and increase residence time (RT) of PTH peptide. Polymeric delivery vehicles and other agents and methods of the present invention that yield sustained release-enhancing formulations, for example, polyethylene glycol (PEG), are disclosed herein. The present invention provides an improved PTH peptide delivery method and dosage form for treatment or prevention of osteoporosis or osteopenia in mammalian subjects.

Within the mucosal delivery formulations and methods of the invention, the PTH peptide is frequently combined or coordinately administered with a suitable carrier or vehicle for mucosal delivery. As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, can be found in the *U.S. Pharmacopeia National Formulary*, 1857-1859, (1990). Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like. The amount of active ingredient that can be combined with the carrier materials to produce a single dosage form will vary depending upon the particular mode of administration.

Within the mucosal delivery compositions and methods of the invention, various delivery-enhancing agents are employed which enhance delivery of PTH peptide into or across a mucosal surface. In this regard, delivery of PTH peptide across the mucosal epithelium can occur "transcellularly" or "paracellularly". The extent to which these pathways contribute to the overall flux and bioavailability of the PTH peptide depends upon the environment of the mucosa, the physico-chemical properties the active agent, and on the properties of the mucosal epithelium. Paracellular transport involves only passive diffusion, whereas transcellular transport can occur by passive, facilitated or active processes. Generally, hydrophilic, passively transported, polar solutes diffuse through the paracellular route, while more lipophilic solutes use the transcellular route. Absorption and bioavailability (e.g., as reflected by a permeability coefficient or physiological assay), for diverse, passively and actively absorbed solutes, can be readily evaluated, in terms of both paracellular and transcellular delivery components, for any selected PTH peptide within the invention. For passively absorbed drugs, the relative contribution of paracellular and transcellular pathways to drug transport depends upon the pKa, partition coefficient, molecular radius and charge of the drug, the pH of the luminal environment in which the drug is delivered, and the area of the absorbing surface. The paracellular route represents a relatively small fraction of accessible surface area of the nasal mucosal epithelium. In general terms, it has been reported that cell membranes occupy a mucosal surface area that is a thousand times greater than the area occupied by the paracellular spaces. Thus, the smaller accessible area, and the size- and charge-based discrimination against macromolecular permeation would suggest that the paracellular route would be a generally less favorable route than transcellular delivery for drug transport. Surprisingly, the methods and compositions of the invention provide for significantly enhanced transport of biotherapeutics into and across mucosal epithelia via the paracellular route. Therefore, the methods and compositions of the invention successfully target both paracellular and transcellular routes, alternatively or within a single method or composition.

As used herein, "mucosal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of PTH peptide or other biologically active compound(s). Enhancement of mucosal delivery can thus occur by any of a variety of mechanisms, for example by increasing the diffusion, transport, persistence or stability of PTH peptide, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

As used herein, a "mucosally effective amount of PTH peptide" contemplates effective mucosal delivery of PTH peptide to a target site for drug activity in the subject that may involve a variety of delivery or transfer routes. For example, a given active agent may find its way through clearances between cells of the mucosa and reach an adjacent vascular wall, while by another route the agent may, either passively or actively, be taken up into mucosal cells to act within the cells or be discharged or transported out of the cells to reach a secondary target site, such as the systemic circulation. The methods and compositions of the invention may promote the translocation of active agents along one or more such alternate routes, or may act directly on the mucosal tissue or proximal vascular tissue to promote absorption or penetration of the active agent(s). The promotion of absorption or penetration in this context is not limited to these mechanisms.

As used herein "peak concentration ($C_{max}$) of PTH peptide in a blood plasma", "area under concentration vs. time curve (AUC) of PTH peptide in a blood plasma", "time to maximal plasma concentration ($t_{max}$) of PTH peptide in a blood plasma" are pharmacokinetic parameters known to one skilled in the art. Laursen et al., *Eur. J. Endocrinology*, 135: 309-315 (1996). The "concentration vs. time curve" measures the concentration of PTH peptide in a blood serum of a subject vs. time after administration of a dosage of PTH peptide to the subject either by intranasal, intramuscular, subcutaneous, or other parenteral route of administration. "$C_{max}$" is the maximum concentration of PTH peptide in the blood serum of a subject following a single dosage of PTH peptide to the subject. "$t_{max}$" is the time to reach maximum concentration of PTH peptide in a blood serum of a subject following administration of a single dosage of PTH peptide to the subject.

While the mechanism of absorption promotion may vary with different mucosal delivery-enhancing agents of the invention, useful reagents in this context will not substantially adversely affect the mucosal tissue and will be selected according to the physicochemical characteristics of the particular PTH peptide or other active or delivery-enhancing agent. In this context, delivery-enhancing agents that increase penetration or permeability of mucosal tissues will often result in some alteration of the protective permeability barrier of the mucosa. For such delivery-enhancing agents to be of value within the invention, it is generally desired that any significant changes in permeability of the mucosa be reversible within a time frame appropriate to the desired duration of drug delivery. Furthermore, there should be no substantial, cumulative toxicity, nor any permanent deleterious changes induced in the barrier properties of the mucosa with long-term use.

Within certain aspects of the invention, absorption-promoting agents for coordinate administration or combinatorial formulation with PTH peptide of the invention are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium laurylsulfate, oleic acid, and the bile salts, may be employed to enhance mucosal penetration of the PTH peptide. In additional aspects, surfactants (e.g., polysorbates) are employed as adjunct compounds, processing agents, or formulation additives to enhance intranasal delivery of the PTH peptide. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the PTH peptide from the vehicle into the mucosa.

Additional mucosal delivery-enhancing agents that are useful within the coordinate administration and processing methods and combinatorial formulations of the invention include, but are not limited to, mixed micelles; enamines; nitric oxide donors (e.g., S-nitroso-N-acetyl-DL-penicillamine, NOR1, NOR4—which are preferably co-administered with an NO scavenger such as carboxy-PITO or doclofenac sodium); sodium salicylate; glycerol esters of acetoacetic acid (e.g., glyceryl-1,3-diacetoacetate or 1,2-isopropylideneglycerine-3-acetoacetate); and other release-diffusion or intra- or trans-epithelial penetration-promoting agents that are physiologically compatible for mucosal delivery. Other absorption-promoting agents are selected from a variety of carriers, bases and excipients that enhance mucosal delivery, stability, activity or trans-epithelial penetration of the PTH peptide. These include, inter alia, cyclodextrins and β-cyclodextrin derivatives (e.g., 2-hydroxypropyl-β-cyclodextrin and heptakis(2,6-di-O-methyl-β-cyclodextrin). These compounds, optionally conjugated with one or more of the active ingredients and further optionally formulated in an oleaginous base, enhance bioavailability in the mucosal formulations of the invention. Yet additional absorption-enhancing agents adapted for mucosal delivery include medium-chain fatty acids, including mono- and diglycerides (e.g., sodium caprate—extracts of coconut oil, Capmul), and triglycerides (e.g., amylodextrin, Estaram 299, Miglyol 810).

The mucosal therapeutic and prophylactic compositions of the present invention may be supplemented with any suitable penetration-promoting agent that facilitates absorption, diffusion, or penetration of PTH peptide across mucosal barriers. The penetration promoter may be any promoter that is pharmaceutically acceptable. Thus, in more detailed aspects of the invention compositions are provided that incorporate one or more penetration-promoting agents selected from sodium salicylate and salicylic acid derivatives (acetyl salicylate, choline salicylate, salicylamide, etc.); amino acids and salts thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc—inclusive of their alkali metal or alkaline earth metal salts); and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts). Also provided as penetration-promoting agents within the methods and compositions of the invention are substances which are generally used as emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like.

Within various aspects of the invention, improved nasal mucosal delivery formulations and methods are provided that allow delivery of PTH peptide and other therapeutic agents within the invention across mucosal barriers between administration and selected target sites. Certain formulations are specifically adapted for a selected target cell, tissue or organ, or even a particular disease state. In other aspects, formulations and methods provide for efficient, selective endo- or transcytosis of PTH peptide specifically routed along a defined intracellular or intercellular pathway. Typically, the PTH peptide is efficiently loaded at effective concentration levels in a carrier or other delivery vehicle, and is delivered and maintained in a stabilized form, e.g., at the nasal mucosa and/or during passage through intracellular compartments and membranes to a remote target site for drug action (e.g., the blood stream or a defined tissue, organ, or extracellular compartment). The PTH peptide may be provided in a delivery vehicle or otherwise modified (e.g., in the form of a prodrug), wherein release or activation of the PTH peptide is triggered by a physiological stimulus (e.g. pH change, lysosomal enzymes, etc.) Often, the PTH peptide is pharmacologically inactive until it reaches its target site for activity. In most cases, the PTH peptide and other formulation components are non-toxic and non-immunogenic. In this context, carriers and other formulation components are generally selected for their ability to be rapidly degraded and excreted under physiological conditions. At the same time, formulations are chemically and physically stable in dosage form for effective storage.

Included within the definition of biologically active peptides and proteins for use within the invention are natural or synthetic, therapeutically or prophylactically active, peptides (comprised of two or more covalently linked amino acids), proteins, peptide or protein fragments, peptide or protein analogs, and chemically modified derivatives or salts of active peptides or proteins. A wide variety of useful analogs and mimetics of PTH peptide are contemplated for use within the invention and can be produced and tested for biological activity according to known methods. Often, the peptides or proteins of PTH peptide or other biologically active peptides or proteins for use within the invention are muteins that are readily obtainable by partial substitution, addition, or deletion of amino acids within a naturally occurring or native (e.g., wild-type, naturally occurring mutant, or allelic variant) peptide or protein sequence. Additionally, biologically active fragments of native peptides or proteins are included. Such mutant derivatives and fragments substantially retain the desired biological activity of the native peptide or proteins. In the case of peptides or proteins having carbohydrate chains, biologically active variants marked by alterations in these carbohydrate species are also included within the invention.

As used herein, the term "conservative amino acid substitution" refers to the general interchangeability of amino acid residues having similar side chains. For example, a commonly interchangeable group of amino acids having aliphatic side chains is alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Examples of conservative substitutions include the substitution of a non-polar (hydrophobic) residue such as isoleucine, valine, leucine or methionine for another. Likewise, the present invention contemplates the substitution of a polar (hydrophilic) residue such as between arginine and lysine, between glutamine and asparagine, and between threonine and serine. Additionally, the substitution of a basic residue such as lysine, arginine or histidine for another or the substitution of an acidic residue such as aspartic acid or glutamic acid for another is also contemplated. Exemplary conservative amino acids substitution groups are: valine-leucine-isoleucine, phenylalanine-tyrosine, lysine-arginine, alanine-valine, and asparagine-glutamine. By aligning a peptide or protein analog optimally with a corresponding native peptide or protein, and by using appropriate assays, e.g., adhesion protein or receptor binding assays, to determine a selected biological activity, one can readily identify operable peptide and protein analogs for use within the methods and compositions of the invention. Operable peptide and protein analogs are typically specifically immunoreactive with antibodies raised to the corresponding native peptide or protein.

An approach for stabilizing solid protein formulations of the invention is to increase the physical stability of purified, e.g., lyophilized, protein. This will inhibit aggregation via hydrophobic interactions as well as via covalent pathways that may increase as proteins unfold. Stabilizing formulations in this context often include polymer-based formulations, for example a biodegradable hydrogel formulation/ delivery system. As noted above, the critical role of water in protein structure, function, and stability is well known. Typically, proteins are relatively stable in the solid state with bulk water removed. However, solid therapeutic protein formulations may become hydrated upon storage at elevated humidities or during delivery from a sustained release composition or device. The stability of proteins generally drops with increasing hydration. Water can also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

Protein preparations containing between about 6% to 28% water are the most unstable. Below this level, the mobility of bound water and protein internal motions are low. Above this level, water mobility and protein motions approach those of full hydration. Up to a point, increased susceptibility toward solid-phase aggregation with increasing hydration has been observed in several systems. However, at higher water content, less aggregation is observed because of the dilution effect.

In accordance with these principles, an effective method for stabilizing peptides and proteins against solid-state aggregation for mucosal delivery is to control the water content in a solid formulation and maintain the water activity in the formulation at optimal levels. This level depends on the nature of the protein, but in general, proteins maintained below their "monolayer" water coverage will exhibit superior solid-state stability.

A variety of additives, diluents, bases and delivery vehicles are provided within the invention that effectively control water content to enhance protein stability. These reagents and carrier materials effective as anti-aggregation agents in this sense include, for example, polymers of various functionalities, such as polyethylene glycol, dextran, diethylaminoethyl dextran, and carboxymethyl cellulose, which significantly increase the stability and reduce the solid-phase aggregation of peptides and proteins admixed therewith or linked thereto. In some instances, the activity or physical stability of proteins can also be enhanced by various additives to aqueous solutions of the peptide or protein drugs. For example, additives, such as polyols (including sugars), amino acids, proteins such as collagen and gelatin, and various salts may be used.

Certain additives, in particular sugars and other polyols, also impart significant physical stability to dry, e.g., lyophilized proteins. These additives can also be used within the invention to protect the proteins against aggregation not only during lyophilization but also during storage in the dry state. For example sucrose and Ficoll 70 (a polymer with sucrose units) exhibit significant protection against peptide or protein aggregation during solid-phase incubation under various conditions. These additives may also enhance the stability of solid proteins embedded within polymer matrices.

Yet additional additives, for example sucrose, stabilize proteins against solid-state aggregation in humid atmospheres at elevated temperatures, as may occur in certain sustained-release formulations of the invention. Proteins such as gelatin and collagen also serve as stabilizing or bulking agents to reduce denaturation and aggregation of unstable proteins in this context. These additives can be incorporated into polymeric melt processes and compositions within the invention. For example, polypeptide microparticles can be prepared by simply lyophilizing or spray drying a solution containing various stabilizing additives described above. Sustained release of unaggregated peptides and proteins can thereby be obtained over an extended period of time.

Various additional preparative components and methods, as well as specific formulation additives, are provided herein which yield formulations for mucosal delivery of aggregation-prone peptides and proteins, wherein the peptide or protein is stabilized in a substantially pure, unaggregated form using a solubilization agent. A range of components and additives are contemplated for use within these methods and formulations. Exemplary of these solubilization agents are cyclodextrins (CDs), which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of protein aggregation provides additional advantages within the intranasal delivery methods and compositions of the invention. Additional agents for use in this context include CD dimers, trimers and tetramers with varying geometries controlled by the linkers that specifically block aggregation of peptides and protein. Yet solubilization agents and methods for incorporation within the invention involve the use of peptides and peptide mimetics to selectively block protein-protein interactions. In one aspect, the specific binding of hydrophobic side chains reported for CD multimers is extended to proteins via the use of peptides and peptide mimetics that similarly block protein aggregation. A wide range of suitable methods and anti-aggregation agents are available for incorporation within the compositions and procedures of the invention.

To improve the transport characteristics of biologically active agents (including PTH peptide, other active peptides and proteins, and macromolecular and small molecule drugs) for enhanced delivery across hydrophobic mucosal membrane barriers, the invention also provides techniques and reagents for charge modification of selected biologically active agents or delivery-enhancing agents described herein. In this regard, the relative permeabilities of macromolecules is generally be related to their partition coefficients. The degree of ionization of molecules, which is dependent on the $pK_a$ of the molecule and the pH at the mucosal membrane surface, also affects permeability of the molecules. Permeation and partitioning of biologically active agents, including PTH peptide and analogs of the invention, for mucosal delivery may be facilitated by charge alteration or charge spreading of the active agent or permeabilizing agent, which is achieved, for example, by alteration of charged functional groups, by modifying the pH of the delivery vehicle or solution in which the active agent is delivered, or by coordinate administration of a charge- or pH-altering reagent with the active agent.

Consistent with these general teachings, mucosal delivery of charged macromolecular species, including PTH peptide and other biologically active peptides and proteins, within the methods and compositions of the invention is substantially improved when the active agent is delivered to the mucosal surface in a substantially unionized, or neutral, electrical charge state.

Certain PTH peptide and other biologically active peptide and protein components of mucosal formulations for use within the invention will be charge modified to yield an increase in the positive charge density of the peptide or protein. These modifications extend also to cationization of peptide and protein conjugates, carriers and other delivery forms disclosed herein. Cationization offers a convenient means of altering the biodistribution and transport properties of proteins and macromolecules within the invention. Cationization is undertaken in a manner that substantially preserves the biological activity of the active agent and limits potentially adverse side effects, including tissue damage and toxicity.

Effective delivery of biotherapeutic agents via intranasal administration must take into account the decreased drug transport rate across the protective mucus lining of the nasal mucosa, in addition to drug loss due to binding to glycoproteins of the mucus layer. Normal mucus is a viscoelastic, gel-like substance consisting of water, electrolytes, mucins, macromolecules, and sloughed epithelial cells. It serves primarily as a cytoprotective and lubricative covering for the underlying mucosal tissues. Mucus is secreted by randomly distributed secretory cells located in the nasal epithelium and in other mucosal epithelia. The structural unit of mucus is mucin. This glycoprotein is mainly responsible for the viscoelastic nature of mucus, although other macromolecules may also contribute to this property. In airway mucus, such macromolecules include locally produced secretory IgA, IgM, IgE, lysozyme, and bronchotransferrin, which also play an important role in host defense mechanisms.

The coordinate administration methods of the instant invention optionally incorporate effective mucolytic or mucus-clearing agents, which serve to degrade, thin or clear mucus from intranasal mucosal surfaces to facilitate absorption of intranasally administered biotherapeutic agents. Within these methods, a mucolytic or mucus-clearing agent is coordinately administered as an adjunct compound to enhance intranasal delivery of the biologically active agent. Alternatively, an effective amount of a mucolytic or mucus-clearing agent is incorporated as a processing agent within a multi-processing method of the invention, or as an additive within a combinatorial formulation of the invention, to provide an improved formulation that enhances intranasal delivery of biotherapeutic compounds by reducing the barrier effects of intranasal mucus.

A variety of mucolytic or mucus-clearing agents are available for incorporation within the methods and compositions of the invention. Based on their mechanisms of action, mucolytic and mucus clearing agents can often be classified into the following groups: proteases (e.g., pronase, papain) that cleave the protein core of mucin glycoproteins; sulfhydryl compounds that split mucoprotein disulfide linkages; and detergents (e.g., Triton X-100, Tween 20) that break non-covalent bonds within the mucus. Additional compounds in this context include, but are not limited to, bile salts and surfactants, for example, sodium deoxycholate, sodium taurodeoxycholate, sodium glycocholate, and lysophosphatidylcholine.

The effectiveness of bile salts in causing structural breakdown of mucus is in the order deoxycholate>taurocholate>glycocholate. Other effective agents that reduce mucus viscosity or adhesion to enhance intranasal delivery according to the methods of the invention include, e.g., short-chain fatty acids, and mucolytic agents that work by chelation, such as N-acylcollagen peptides, bile acids, and saponins (the latter function in part by chelating $Ca^{2+}$ and/or $Mg^{2+}$ which play an important role in maintaining mucus layer structure).

Additional mucolytic agents for use within the methods and compositions of the invention include N-acetyl-L-cysteine (ACS), a potent mucolytic agent that reduces both the viscosity and adherence of bronchopulmonary mucus and is reported to modestly increase nasal bioavailability of human growth hormone in anesthetized rats (from 7.5 to 12.2%). These and other mucolytic or mucus-clearing agents are contacted with the nasal mucosa, typically in a concentration range of about 0.2 to 20 mM, coordinately with administration of the biologically active agent, to reduce the polar viscosity and/or elasticity of intranasal mucus.

Still other mucolytic or mucus-clearing agents may be selected from a range of glycosidase enzymes, which are able to cleave glycosidic bonds within the mucus glycoprotein. α-amylase and β-amylase are representative of this class of enzymes, although their mucolytic effect may be limited. In contrast, bacterial glycosidases which allow these microorganisms to permeate mucus layers of their hosts.

For combinatorial use with most biologically active agents within the invention, including peptide and protein therapeutics, non-ionogenic detergents are generally also useful as mucolytic or mucus-clearing agents. These agents typically will not modify or substantially impair the activity of therapeutic polypeptides.

Because the self-cleaning capacity of certain mucosal tissues (e.g., nasal mucosal tissues) by mucociliary clearance is necessary as a protective function (e.g., to remove dust, allergens, and bacteria), it has been generally considered that this function should not be substantially impaired by mucosal medications. Mucociliary transport in the respiratory tract is a particularly important defense mechanism against infections. To achieve this function, ciliary beating in the nasal and airway passages moves a layer of mucus along the mucosa to removing inhaled particles and microorganisms.

Ciliostatic agents find use within the methods and compositions of the invention to increase the residence time of mucosally (e.g., intranasally) administered PTH peptide, analogs and mimetics, and other biologically active agents disclosed herein. In particular, the delivery these agents within the methods and compositions of the invention is significantly enhanced in certain aspects by the coordinate administration or combinatorial formulation of one or more ciliostatic agents that function to reversibly inhibit ciliary activity of mucosal cells, to provide for a temporary, reversible increase in the residence time of the mucosally administered active agent(s). For use within these aspects of the invention, the foregoing ciliostatic factors, either specific or indirect in their activity, are all candidates for successful employment as ciliostatic agents in appropriate amounts (depending on concentration, duration and mode of delivery) such that they yield a transient (i.e., reversible) reduction or cessation of mucociliary clearance at a mucosal site of administration to enhance delivery of PTH peptide, analogs and mimetics, and other biologically active agents disclosed herein, without unacceptable adverse side effects.

Within more detailed aspects, a specific ciliostatic factor is employed in a combined formulation or coordinate administration protocol with one or more PTH peptide proteins, analogs and mimetics, and/or other biologically active agents disclosed herein. Various bacterial ciliostatic factors isolated and characterized in the literature may be employed within these embodiments of the invention. Ciliostatic factors from the bacterium *Pseudomonas aeruginosa* include a phenazine derivative, a pyo compound (2-alkyl-4-hydroxyquinolines), and a rhamnolipid (also known as a hemolysin). The pyo compound produced ciliostasis at concentrations of 50 μg/ml and without obvious ultrastructural lesions. The phenazine derivative also inhibited ciliary motility but caused some membrane disruption, although at substantially greater concentrations of 400 μg/ml. Limited exposure of tracheal explants to the rhamnolipid resulted in ciliostasis, which was associated with altered ciliary membranes. More extensive exposure to rhamnolipid was associated with removal of dynein arms from axonemes.

Within more detailed aspects of the invention, one or more membrane penetration-enhancing agents may be employed within a mucosal delivery method or formulation of the invention to enhance mucosal delivery of PTH peptide analogs and mimetics, and other biologically active agents disclosed herein. Membrane penetration enhancing agents in this context can be selected from: (i) a surfactant, (ii) a bile salt, (iii) a phospholipid additive, mixed micelle, liposome, or carrier, (iv) an alcohol, (v) an enamine, (vi) an NO donor compound, (vii) a long-chain amphipathic molecule (viii) a small hydrophobic penetration enhancer; (ix) sodium or a salicylic acid derivative; (x) a glycerol ester of acetoacetic acid (xi) a clyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, or (xviii) an inhibitor of cholesterol synthesis; or (xix) any combination of the membrane penetration enhancing agents recited in (i)-(xix).

Certain surface-active agents are readily incorporated within the mucosal delivery formulations and methods of the invention as mucosal absorption enhancing agents. These agents, which may be coordinately administered or combinatorially formulated with PTH peptide proteins, analogs and mimetics, and other biologically active agents disclosed herein, may be selected from a broad assemblage of known surfactants. Surfactants, which generally fall into three classes: (1) nonionic polyoxyethylene ethers; (2) bile salts such as sodium glycocholate (SGC) and deoxycholate (DOC); and (3) derivatives of fusidic acid such as sodium taurodihydrofusidate (STDHF). The mechanisms of action of these various classes of surface-active agents typically include solubilization of the biologically active agent. For proteins and peptides which often form aggregates, the surface active properties of these absorption promoters can allow interactions with proteins such that smaller units such as surfactant coated monomers may be more readily maintained in solution. Examples of other surface-active agents are L-α-Phosphatidylcholine Didecanoyl (DDPC) polysorbate 80 and polysorbate 20. These monomers are presumably more transportable units than aggregates. A second potential mechanism is the protection of the peptide or protein from proteolytic degradation by proteases in the mucosal environment. Both bile salts and some fusidic acid derivatives reportedly inhibit proteolytic degradation of proteins by nasal homogenates at concentrations less than or equivalent to those required to enhance protein absorption. This protease inhibition may be especially important for peptides with short biological half-lives.

The present invention provides pharmaceutical composition that contains one or more PTH peptides, analogs or mimetics, and/or other biologically active agents in combination with mucosal delivery enhancing agents disclosed herein formulated in a pharmaceutical preparation for mucosal delivery.

The permeabilizing agent reversibly enhances mucosal epithelial paracellular transport, typically by modulating epithelial junctional structure and/or physiology at a mucosal epithelial surface in the subject. This effect typically involves inhibition by the permeabilizing agent of homotypic or heterotypic binding between epithelial membrane adhesive proteins of neighboring epithelial cells. Target proteins for this blockade of homotypic or heterotypic binding can be selected from various related junctional adhesion molecules (JAMs), occludins, or claudins. Examples of this are antibodies, antibody fragments or single-chain antibodies that bind to the extracellular domains of these proteins.

In yet additional detailed embodiments, the invention provides permeabilizing peptides and peptide analogs and mimetics for enhancing mucosal epithelial paracellular transport. The subject peptides and peptide analogs and mimetics typically work within the compositions and methods of the invention by modulating epithelial junctional structure and/or physiology in a mammalian subject. In certain embodiments, the peptides and peptide analogs and mimetics effectively inhibit homotypic and/or heterotypic binding of an epithelial membrane adhesive protein selected from a junctional adhesion molecule (JAM), occludin, or claudin.

One such agent that has been extensively studied is the bacterial toxin from *Vibrio cholerae* known as the "zonula occludens toxin" (ZOT). This toxin mediates increased intestinal mucosal permeability and causes disease symptoms including diarrhea in infected subjects. Fasano et al, *Proc. Nat. Acad. Sci., U.S.A.*, 8:5242-5246 (1991). When tested on rabbit ileal mucosa, ZOT increased the intestinal permeability by modulating the structure of intercellular tight junctions. More recently, it has been found that ZOT is capable of reversibly opening tight junctions in the intestinal mucosa. It has also been reported that ZOT is capable of reversibly opening tight junctions in the nasal mucosa. U.S. Pat. No. 5,908,825.

Within the methods and compositions of the invention, ZOT, as well as various analogs and mimetics of ZOT that function as agonists or antagonists of ZOT activity, are useful for enhancing intranasal delivery of biologically active agents—by increasing paracellular absorption into and across the nasal mucosa. In this context, ZOT typically acts by causing a structural reorganization of tight junctions marked by altered localization of the junctional protein ZO1. Within these aspects of the invention, ZOT is coordinately administered or combinatorially formulated with the biologically active agent in an effective amount to yield significantly enhanced absorption of the active agent, by reversibly increasing nasal mucosal permeability without substantial adverse side effects The compositions and delivery methods of the invention optionally incorporate a selective transport-enhancing agent that facilitates transport of one or more biologically active agents. These transport-enhancing agents may be employed in a combinatorial formulation or coordinate administration protocol with one or more of the PTH peptides, analogs and mimetics disclosed herein, to coordinately enhance delivery of one or more additional biologically active agent(s) across mucosal transport barriers, to enhance mucosal delivery of the active agent(s) to reach a target tissue or compartment in the subject (e.g., the mucosal epithelium, liver, CNS tissue or fluid, or blood plasma). Alternatively, the transport-enhancing agents may be employed in a combinatorial formulation or coordinate administration protocol to directly enhance mucosal delivery of one or more of the PTH peptides, analogs and mimetics, with or without enhanced delivery of an additional biologically active agent.

Exemplary selective transport-enhancing agents for use within this aspect of the invention include, but are not limited to, glycosides, sugar-containing molecules, and binding agents such as lectin binding agents, which are known to interact specifically with epithelial transport barrier components. For example, specific "bioadhesive" ligands, including various plant and bacterial lectins, which bind to cell surface sugar moieties by receptor-mediated interactions can be employed as carriers or conjugated transport mediators for enhancing mucosal, e.g., nasal delivery of biologically active agents within the invention. Certain bioadhesive ligands for use within the invention will mediate transmission of biological signals to epithelial target cells that trigger selective uptake of the adhesive ligand by specialized cellular transport processes (endocytosis or transcytosis). These transport mediators can therefore be employed as a "carrier system" to stimulate or direct selective uptake of one or more PTH peptides, analogs and mimetics, and other biologically active agent(s) into and/or through mucosal epithelia. These and other selective transport-enhancing agents significantly enhance mucosal delivery of macromolecular biopharmaceuticals (particularly peptides, proteins, oligonucleotides and polynucleotide vectors) within the invention. Lectins are plant proteins that bind to specific sugars found on the surface of glycoproteins and glycolipids of eukaryotic cells. Concentrated solutions of lectins have a 'mucotractive' effect, and various studies have demonstrated rapid receptor mediated endocytocis (RME) of lectins and lectin conjugates (e.g., concanavalin A conjugated with colloidal gold particles) across mucosal surfaces. Additional studies have reported that the uptake mechanisms for lectins can be utilized for intestinal drug targeting in vivo. In certain of these studies, polystyrene nanoparticles (500 nm) were covalently coupled to tomato lectin and reported yielded improved systemic uptake after oral administration to rats.

In addition to plant lectins, microbial adhesion and invasion factors provide a rich source of candidates for use as adhesive/selective transport carriers within the mucosal delivery methods and compositions of the invention. Two components are necessary for bacterial adherence processes, a bacterial 'adhesin' (adherence or colonization factor) and a receptor on the host cell surface. Bacteria causing mucosal infections need to penetrate the mucus layer before attaching themselves to the epithelial surface. This attachment is usually mediated by bacterial fimbriae or pilus structures, although other cell surface components may also take part in the process. Adherent bacteria colonize mucosal epithelia by multiplication and initiation of a series of biochemical reactions inside the target cell through signal transduction mechanisms (with or without the help of toxins). Associated with these invasive mechanisms, a wide diversity of bioadhesive proteins (e.g., invasin, internalin) originally produced by various bacteria and viruses are known. These allow for extracellular attachment of such microorganisms with an impressive selectivity for host species and even particular target tissues. Signals transmitted by such receptor-ligand interactions trigger the transport of intact, living microorganisms into, and eventually through, epithelial cells by endo- and transcytotic processes. Such naturally occurring phenomena may be harnessed (e.g., by complexing biologically active agents such as PTH peptides with an adhesin) according to the teachings herein for enhanced delivery of biologically active compounds into or across mucosal epithelia and/or to other designated target sites of drug action.

Various bacterial and plant toxins that bind epithelial surfaces in a specific, lectin-like manner are also useful within the methods and compositions of the invention. For example, diptheria toxin (DT) enters host cells rapidly by RME. Likewise, the B subunit of the E. coli heat labile toxin binds to the brush border of intestinal epithelial cells in a highly specific, lectin-like manner. Uptake of this toxin and transcytosis to the basolateral side of the enterocytes has been reported in vivo and in vitro. Other researches have expressed the transmembrane domain of diphtheria toxin in E. coli as a maltose-binding fusion protein and coupled it chemically to high-Mw poly-L-lysine. The resulting complex was successfully used to mediate internalization of a reporter gene in vitro. In addition to these examples, Staphylococcus aureus produces a set of proteins (e.g., staphylococcal enterotoxin A (SEA), SEB, toxic shock syndrome toxin 1 (TSST-1) which act both as superantigens and toxins. Studies relating to these proteins have reported dose-dependent, facilitated transcytosis of SEB and TSST-I in Caco-2 cells.

Viral haemagglutinins comprise another type of transport agent to facilitate mucosal delivery of biologically active agents within the methods and compositions of the invention. The initial step in many viral infections is the binding of surface proteins (haemagglutinins) to mucosal cells. These binding proteins have been identified for most viruses, including rotaviruses, varicella zoster virus, semliki forest virus, adenoviruses, potato leafroll virus, and reovirus. These and other exemplary viral hemagglutinins can be employed in a combinatorial formulation (e.g., a mixture or conjugate formulation) or coordinate administration protocol with one or more of the PTH peptide, analogs and mimetics disclosed herein, to coordinately enhance mucosal delivery of one or more additional biologically active agent (s). Alternatively, viral hemagglutinins can be employed in a combinatorial formulation or coordinate administration protocol to directly enhance mucosal delivery of one or more of the PTH peptide proteins, analogs and mimetics, with or without enhanced delivery of an additional biologically active agent.

A variety of endogenous, selective transport-mediating factors are also available for use within the invention. Mammalian cells have developed an assortment of mechanisms to facilitate the internalization of specific substrates and target these to defined compartments. Collectively, these processes of membrane deformations are termed 'endocytosis' and comprise phagocytosis, pinocytosis, receptor-mediated endocytosis (clathrin-mediated RME), and potocytosis (non-clathrin-mediated RME). RME is a highly specific cellular biologic process by which, as its name implies, various ligands bind to cell surface receptors and are subsequently internalized and trafficked within the cell. In many cells the process of endocytosis is so active that the entire membrane surface is internalized and replaced in less than a half hour. Two classes of receptors are proposed based on their orientation in the cell membrane; the amino terminus of Type I receptors is located on the extracellular side of the membrane, whereas Type II receptors have this same protein tail in the intracellular milieu.

Still other embodiments of the invention utilize transferrin as a carrier or stimulant of RME of mucosally delivered biologically active agents. Transferrin, an 80 kDa iron-transporting glycoprotein, is efficiently taken up into cells by RME. Transferrin receptors are found on the surface of most proliferating cells, in elevated numbers on erythroblasts and on many kinds of tumors. The transcytosis of transferrin (Tf) and transferrin conjugates is reportedly enhanced in the presence of Brefeldin A (BFA), a fungal metabolite. In other studies, BFA treatment has been reported to rapidly increase apical endocytosis of both ricin and HRP in MDCK cells. Thus, BFA and other agents that stimulate receptor-mediated transport can be employed within the methods of the invention as combinatorially formulated (e.g., conjugated) and/or coordinately administered agents to enhance receptor-mediated transport of biologically active agents, including PTH peptide proteins, analogs and mimetics.

In certain aspects of the invention, the combinatorial formulations and/or coordinate administration methods herein incorporate an effective amount of peptides and proteins which may adhere to charged glass thereby reducing the effective concentration in the container. Silanized containers, for example, silanized glass containers, are used to store the finished product to reduce adsorption of the polypeptide or protein to a glass container.

In yet additional aspects of the invention, a kit for treatment of a mammalian subject comprises a stable pharmaceutical composition of one or more PTH peptide compound(s) formulated for mucosal delivery to the mammalian subject wherein the composition is effective for treating or preventing osteoporosis or osteopenia. The kit further comprises a pharmaceutical reagent vial to contain the one or more PTH peptide compounds. The pharmaceutical reagent vial is composed of pharmaceutical grade polymer, glass or other suitable material. The pharmaceutical reagent vial is, for example, a silanized glass vial. The kit further comprises an aperture for delivery of the composition to a nasal mucosal surface of the subject. The delivery aperture is composed of a pharmaceutical grade polymer, glass or other suitable material. The delivery aperture is, for example, a silanized glass.

A silanization technique combines a special cleaning technique for the surfaces to be silanized with a silanization process at low pressure. The silane is in the gas phase and at an enhanced temperature of the surfaces to be silanized. The method provides reproducible surfaces with stable, homogeneous and functional silane layers having characteristics of a monolayer. The silanized surfaces prevent binding to the glass of polypeptides or mucosal delivery enhancing agents of the present invention.

The procedure is useful to prepare silanized pharmaceutical reagent vials to hold PTH peptide compositions of the present invention. Glass trays are cleaned by rinsing with double distilled water (ddH$_2$O) before using. The silane tray is then be rinsed with 95% EtOH, and the acetone tray is rinsed with acetone. Pharmaceutical reagent vials are sonicated in acetone for 10 minutes. After the acetone sonication, reagent vials are washed in ddH$_2$O tray at least twice. Reagent vials are sonicated in 0.1 M NaOH for 10 minutes. While the reagent vials are sonicating in NaOH, the silane solution is made under a hood. (Silane solution: 800 mL of 95% ethanol; 96 L of glacial acetic acid; 25 mL of glycidoxypropyltrimethoxy silane). After the NaOH sonication, reagent vials are washed in ddH$_2$O tray at least twice. The reagent vials are sonicated in silane solution for 3 to 5 minutes. The reagent vials are washed in 100% EtOH tray. The reagent vials are dried with prepurified N$_2$ gas and stored in a 100° C. oven for at least 2 hours before using.

In certain aspects of the invention, the combinatorial formulations and/or coordinate administration methods herein incorporate an effective amount of a nontoxic bioadhesive as an adjunct compound or carrier to enhance mucosal delivery of one or more biologically active agent(s). Bioadhesive agents in this context exhibit general or specific adhesion to one or more components or surfaces of the targeted mucosa. The bioadhesive maintains a desired concentration gradient of the biologically active agent into or across the mucosa to ensure penetration of even large molecules (e.g., peptides and proteins) into or through the mucosal epithelium. Typically, employment of a bioadhesive within the methods and compositions of the invention yields a two- to five-fold, often a five- to ten-fold increase in permeability for peptides and proteins into or through the mucosal epithelium. This enhancement of epithelial permeation often permits effective transmucosal delivery of large macromolecules, for example to the basal portion of the nasal epithelium or into the adjacent extracellular compartments or a blood plasma or CNS tissue or fluid.

This enhanced delivery provides for greatly improved effectiveness of delivery of bioactive peptides, proteins and other macromolecular therapeutic species. These results will depend in part on the hydrophilicity of the compound, whereby greater penetration will be achieved with hydrophilic species compared to water insoluble compounds. In addition to these effects, employment of bioadhesives to enhance drug persistence at the mucosal surface can elicit a reservoir mechanism for protracted drug delivery, whereby compounds not only penetrate across the mucosal tissue but also back-diffuse toward the mucosal surface once the material at the surface is depleted.

A variety of suitable bioadhesives are disclosed in the art for oral administration, U.S. Pat. Nos. 3,972,995; 4,259,314; 4,680,323; 4,740,365; 4,573,996; 4,292,299; 4,715,369; 4,876,092; 4,855,142; 4,250,163; 4,226,848; 4,948,580; U.S. Patent Reissue 33,093, hereby incorporated by reference, which find use within the novel methods and compositions of the invention. The potential of various bioadhesive polymers as a mucosal, e.g., nasal, delivery platform within the methods and compositions of the invention can be readily assessed by determining their ability to retain and release PTH peptide, as well as by their capacity to interact with the mucosal surfaces following incorporation of the active agent therein. In addition, well known methods will be applied to determine the biocompatibility of selected polymers with the tissue at the site of mucosal administration. When the target mucosa is covered by mucus (i.e., in the absence of mucolytic or mucus-clearing treatment), it can serve as a connecting link to the underlying mucosal epithelium. Therefore, the term "bioadhesive" as used herein also covers mucoadhesive compounds useful for enhancing mucosal delivery of biologically active agents within the invention. However, adhesive contact to mucosal tissue mediated through adhesion to a mucus gel layer may be limited by incomplete or transient attachment between the mucus layer and the underlying tissue, particularly at nasal surfaces where rapid mucus clearance occurs. In this regard, mucin glycoproteins are continuously secreted and, immediately after their release from cells or glands, form a viscoelastic gel. The luminal surface of the adherent gel layer, however, is continuously eroded by mechanical, enzymatic and/or ciliary action. Where such activities are more prominent or where longer adhesion times are desired, the coordinate administration methods and combinatorial formulation methods of the invention may further incorporate mucolytic and/or ciliostatic methods or agents as disclosed herein above.

Typically, mucoadhesive polymers for use within the invention are natural or synthetic macromolecules which adhere to wet mucosal tissue surfaces by complex, but non-specific, mechanisms. In addition to these mucoadhesive polymers, the invention also provides methods and compositions incorporating bioadhesives that adhere directly to a cell surface, rather than to mucus, by means of specific, including receptor-mediated, interactions. One example of bioadhesives that function in this specific manner is the group of compounds known as lectins. These are glycoproteins with an ability to specifically recognize and bind to sugar molecules, e.g. glycoproteins or glycolipids, which form part of intranasal epithelial cell membranes and can be considered as "lectin receptors".

In certain aspects of the invention, bioadhesive materials for enhancing intranasal delivery of biologically active agents comprise a matrix of a hydrophilic, e.g., water soluble or swellable, polymer or a mixture of polymers that can adhere to a wet mucous surface. These adhesives may be formulated as ointments, hydrogels (see above) thin films, and other application forms. Often, these adhesives have the biologically active agent mixed therewith to effectuate slow release or local delivery of the active agent. Some are formulated with additional ingredients to facilitate penetration of the active agent through the nasal mucosa, e.g., into the circulatory system of the individual.

Various polymers, both natural and synthetic ones, show significant binding to mucus and/or mucosal epithelial surfaces under physiological conditions. The strength of this interaction can readily be measured by mechanical peel or shear tests. When applied to a humid mucosal surface, many dry materials will spontaneously adhere, at least slightly. After such an initial contact, some hydrophilic materials start to attract water by adsorption, swelling or capillary forces, and if this water is absorbed from the underlying substrate or from the polymer-tissue interface, the adhesion may be sufficient to achieve the goal of enhancing mucosal absorption of biologically active agents. Such 'adhesion by hydration' can be quite strong, but formulations adapted to employ this mechanism must account for swelling which continues as the dosage transforms into a hydrated mucilage. This is projected for many hydrocolloids useful within the invention, especially some cellulose-derivatives, which are generally non-adhesive when applied in pre-hydrated state. Nevertheless, bioadhesive drug delivery systems for mucosal administration are effective within the invention when such materials are applied in the form of a dry polymeric powder, microsphere, or film-type delivery form.

Other polymers adhere to mucosal surfaces not only when applied in dry, but also in fully hydrated state, and in the presence of excess amounts of water. The selection of a mucoadhesive thus requires due consideration of the conditions, physiological as well as physico-chemical, under which the contact to the tissue will be formed and maintained. In particular, the amount of water or humidity usually present at the intended site of adhesion, and the prevailing pH, are known to largely affect the mucoadhesive binding strength of different polymers.

Several polymeric bioadhesive drug delivery systems have been fabricated and studied in the past 20 years, not always with success. A variety of such carriers are, however, currently used in clinical applications involving dental, orthopedic, ophthalmological, and surgical uses. For example, acrylic-based hydrogels have been used extensively for bioadhesive devices. Acrylic-based hydrogels are well suited for bioadhesion due to their flexibility and nonabrasive characteristics in the partially swollen state, which reduce damage-causing attrition to the tissues in contact. Furthermore, their high permeability in the swollen state allows unreacted monomer, un-crosslinked polymer chains, and the initiator to be washed out of the matrix after polymerization, which is an important feature for selection of bioadhesive materials for use within the invention. Acrylic-based polymer devices exhibit very high adhesive bond strength. For controlled mucosal delivery of peptide and protein drugs, the methods and compositions of the invention optionally include the use of carriers, e.g., polymeric delivery vehicles that function in part to shield the biologically active agent from proteolytic breakdown, while at the same time providing for enhanced penetration of the peptide or protein into or through the nasal mucosa. In this context, bioadhesive polymers have demonstrated considerable potential for enhancing oral drug delivery. As an example, the bioavailability of 9-desglycinamide, 8-arginine vasopressin (DGAVP) intraduodenally administered to rats together with a 1% (w/v) saline dispersion of the mucoadhesive poly(acrylic acid) derivative polycarbophil, was 3-5-fold increased compared to an aqueous solution of the peptide drug without this polymer.

Mucoadhesive polymers of the poly(acrylic acid)-type are potent inhibitors of some intestinal proteases. The mechanism of enzyme inhibition is explained by the strong affinity of this class of polymers for divalent cations, such as calcium or zinc, which are essential cofactors of metalloproteinases, such as trypsin and chymotrypsin. Depriving the proteases of their cofactors by poly(acrylic acid) was reported to induce irreversible structural changes of the enzyme proteins which were accompanied by a loss of enzyme activity. At the same time, other mucoadhesive polymers (e.g., some cellulose derivatives and chitosan) may not inhibit proteolytic enzymes under certain conditions. In contrast to other enzyme inhibitors contemplated for use within the invention (e.g. aprotinin, bestatin), which are relatively small molecules, the trans-nasal absorption of inhibitory polymers is likely to be minimal in light of the size of these molecules, and thereby eliminate possible adverse side effects. Thus, mucoadhesive polymers, particularly of the poly(acrylic acid)-type, may serve both as an absorption-promoting adhesive and enzyme-protective agent to enhance controlled delivery of peptide and protein drugs, especially when safety concerns are considered.

In addition to protecting against enzymatic degradation, bioadhesives and other polymeric or non-polymeric absorption-promoting agents for use within the invention may directly increase mucosal permeability to biologically active agents. To facilitate the transport of large and hydrophilic molecules, such as peptides and proteins, across the nasal epithelial barrier, mucoadhesive polymers and other agents have been postulated to yield enhanced permeation effects beyond what is accounted for by prolonged premucosal residence time of the delivery system. The time course of drug plasma concentrations reportedly suggested that the bioadhesive microspheres caused an acute, but transient increase of insulin permeability across the nasal mucosa. Other mucoadhesive polymers for use within the invention, for example chitosan, reportedly enhance the permeability of certain mucosal epithelia even when they are applied as an aqueous solution or gel. Another mucoadhesive polymer reported to directly affect epithelial permeability is hyaluronic acid and ester derivatives thereof. A particularly useful bioadhesive agent within the coordinate administration, and/or combinatorial formulation methods and compositions of the invention is chitosan, as well as its analogs and derivatives. Chitosan is a non-toxic, biocompatible and biodegradable polymer that is widely used for pharmaceutical and medical applications because of its favorable properties of low toxicity and good biocompatibility. It is a natural polyaminosaccharide prepared from chitin by N-deacetylation with alkali. As used within the methods and compositions of the invention, chitosan increases the retention of PTH peptides, analogs and mimetics, and other biologically active agents disclosed herein at a mucosal site of application. This mode of administration can also improve patient compliance and acceptance. As further provided herein, the methods and compositions of the invention will optionally include a novel chitosan derivative or chemically modified form of chitosan. One such novel derivative for use within the invention is denoted as a $\beta$-[1→4]-2-guanidino-2-deoxy- D-glucose polymer (poly-GuD). Chitosan is the N-deacetylated product of chitin, a naturally occurring polymer that has been used extensively to prepare microspheres for oral and intra-nasal formulations. The chitosan polymer has also been proposed as a soluble carrier for parenteral drug delivery. Within one aspect of the invention, o-methylisourea is used to convert a chitosan amine to its guanidinium moiety. The guanidinium compound is prepared, for example, by the reaction between equi-normal solutions of chitosan and o-methylisourea at pH above 8.0.

The guanidinium product is -[14]-guanidino-2-deoxy-D-glucose polymer. It is abbreviated as Poly-GuD in this context (Monomer F.W. of Amine in Chitosan=161; Monomer F.W. of Guanidinium in Poly-GuD=203).

Additional compounds classified as bioadhesive agents for use within the present invention act by mediating specific interactions, typically classified as "receptor-ligand interactions" between complementary structures of the bioadhesive compound and a component of the mucosal epithelial surface. Many natural examples illustrate this form of specific binding bioadhesion, as exemplified by lectin-sugar interactions. Lectins are (glyco) proteins of non-immune origin which bind to polysaccharides or glycoconjugates.

Several plant lectins have been investigated as possible pharmaceutical absorption-promoting agents. One plant lectin, *Phaseolus vulgaris* hemagglutinin (PHA), exhibits high oral bioavailability of more than 10% after feeding to rats. Tomato (*Lycopersicon esculeutum*) lectin (TL) appears safe for various modes of administration.

In summary, the foregoing bioadhesive agents are useful in the combinatorial formulations and coordinate administration methods of the instant invention, which optionally incorporate an effective amount and form of a bioadhesive agent to prolong persistence or otherwise increase mucosal absorption of one or more PTH peptides, analogs and mimetics, and other biologically active agents. The bioadhesive agents may be coordinately administered as adjunct compounds or as additives within the combinatorial formulations of the invention. In certain embodiments, the bioadhesive agent acts as a 'pharmaceutical glue', whereas in other embodiments adjunct delivery or combinatorial formulation of the bioadhesive agent serves to intensify contact of the biologically active agent with the nasal mucosa, in some cases by promoting specific receptor-ligand interactions with epithelial cell "receptors", and in others by increasing epithelial permeability to significantly increase the drug concentration gradient measured at a target site of delivery (e.g., liver, blood plasma, or CNS tissue or fluid). Yet additional bioadhesive agents for use within the invention act as enzyme (e.g., protease) inhibitors to enhance the stability of mucosally administered biotherapeutic agents delivered coordinately or in a combinatorial formulation with the bioadhesive agent.

The coordinate administration methods and combinatorial formulations of the instant invention optionally incorporate effective lipid or fatty acid based carriers, processing agents, or delivery vehicles, to provide improved formulations for mucosal delivery of PTH peptides, analogs and mimetics, and other biologically active agents. For example, a variety of formulations and methods are provided for mucosal delivery which comprise one or more of these active agents, such as a peptide or protein, admixed or encapsulated by, or coordinately administered with, a liposome, mixed micellar carrier, or emulsion, to enhance chemical and physical stability and increase the half life of the biologically active agents (e.g., by reducing susceptibility to proteolysis, chemical modification and/or denaturation) upon mucosal delivery.

Within certain aspects of the invention, specialized delivery systems for biologically active agents comprise small lipid vesicles known as liposomes. These are typically made from natural, biodegradable, non-toxic, and non-immunogenic lipid molecules, and can efficiently entrap or bind drug molecules, including peptides and proteins, into, or onto, their membranes. The attractiveness of liposomes as a peptide and protein delivery system within the invention is increased by the fact that the encapsulated proteins can remain in their preferred aqueous environment within the vesicles, while the liposomal membrane protects them against proteolysis and other destabilizing factors. Even though not all liposome preparation methods known are feasible in the encapsulation of peptides and proteins due to their unique physical and chemical properties, several methods allow the encapsulation of these macromolecules without substantial deactivation.

A variety of methods are available for preparing liposomes for use within the invention, U.S. Pat. Nos. 4,235,871, 4,501,728, and 4,837,028, hereby incorporated by reference. For use with liposome delivery, the biologically active agent is typically entrapped within the liposome, or lipid vesicle, or is bound to the outside of the vesicle.

Like liposomes, unsaturated long chain fatty acids, which also have enhancing activity for mucosal absorption, can form closed vesicles with bilayer-like structures (so called "ufasomes"). These can be formed, for example, using oleic acid to entrap biologically active peptides and proteins for mucosal, e.g., intranasal, delivery within the invention.

Other delivery systems for use within the invention combine the use of polymers and liposomes to ally the advantageous properties of both vehicles such as encapsulation inside the natural polymer fibrin. In addition, release of biotherapeutic compounds from this delivery system is controllable through the use of covalent crosslinking and the addition of antifibrinolytic agents to the fibrin polymer.

More simplified delivery systems for use within the invention include the use of cationic lipids as delivery vehicles or carriers, which can be effectively employed to provide an electrostatic interaction between the lipid carrier and such charged biologically active agents as proteins and polyanionic nucleic acids. This allows efficient packaging of the drugs into a form suitable for mucosal administration and/or subsequent delivery to systemic compartments.

Additional delivery vehicles for use within the invention include long and medium chain fatty acids, as well as surfactant mixed micelles with fatty acids. Most naturally occurring lipids in the form of esters have important implications with regard to their own transport across mucosal surfaces. Free fatty acids and their monoglycerides which have polar groups attached, have been demonstrated in the form of mixed micelles to act on the intestinal barrier as penetration enhancers. This discovery of barrier modifying function of free fatty acids (carboxylic acids with a chain length varying from 12 to 20 carbon atoms) and their polar derivatives has stimulated extensive research on the application of these agents as mucosal absorption enhancers.

For use within the methods of the invention, long chain fatty acids, especially fusogenic lipids (unsaturated fatty acids and monoglycerides such as oleic acid, linoleic acid, linoleic acid, monoolein, etc.) provide useful carriers to enhance mucosal delivery of PTH peptide, analogs and mimetics, and other biologically active agents disclosed herein. Medium chain fatty acids (C6 to C 12) and monoglycerides have also been shown to have enhancing activity in intestinal drug absorption and can be adapted for use within the mocosal delivery formulations and methods of the invention. In addition, sodium salts of medium and long chain fatty acids are effective delivery vehicles and absorption-enhancing agents for mucosal delivery of biologically active agents within the invention. Thus, fatty acids can be employed in soluble forms of sodium salts or by the addition of non-toxic surfactants, e.g., polyoxyethylated hydrogenated castor oil, sodium taurocholate, etc. Other fatty acid and mixed micellar preparations that are useful within the invention include, but are not limited to, Na caprylate (C8), Na caprate (C10), Na laurate (C12) or Na oleate (C18), optionally combined with bile salts, such as glycocholate and taurocholate.

Additional methods and compositions provided within the invention involve chemical modification of biologically active peptides and proteins by covalent attachment of polymeric materials, for example dextrans, polyvinyl pyrrolidones, glycopeptides, polyethylene glycol and polyamino acids. The resulting conjugated peptides and proteins retain their biological activities and solubility for mucosal administration. In alternate embodiments, PTH peptide proteins, analogs and mimetics, and other biologically active peptides and proteins, are conjugated to polyalkylene oxide polymers, particularly polyethylene glycols (PEG). U.S. Pat. No. 4,179,337, hereby incorporated by reference.

Peptides could be linked to PEG directly as described in the art. PEG can be a molecule having a molecular mass ranging between 300 and 60,000. Also included are various PEG molecules, including linear, branched, attached to a peptide at a single moiety or multiple attachment sites. Amine-reactive PEG polymers for use within the invention include SC-PEG with molecular masses of 2000, 5000, 10000, 12000, and 20 000; U-PEG-10000; NHS-PEG-3400-biotin; T-PEG-5000; T-PEG-12000; and TPC-PEG-5000. PEGylation of biologically active peptides and proteins may be achieved by modification of carboxyl sites (e.g., aspartic acid or glutamic acid groups in addition to the carboxyl terminus). The utility of PEG-hydrazide in selective modification of carbodiimide-activated protein carboxyl groups under acidic conditions has been described. Alternatively, bifunctional PEG modification of biologically active peptides and proteins can be employed. In some procedures, charged amino acid residues, including lysine, aspartic acid, and glutamic acid, have a marked tendency to be solvent accessible on protein surfaces.

In addition to PEGylation, biologically active agents such as peptides and proteins for use within the invention can be modified to enhance circulating half-life by shielding the active agent via conjugation to other known protecting or stabilizing compounds, for example by the creation of fusion proteins with an active peptide, protein, analog or mimetic linked to one or more carrier proteins, such as one or more immunoglobulin chains.

Mucosal delivery formulations of the present invention comprise PTH peptides, analogs and mimetics, typically combined together with one or more pharmaceutically acceptable carriers and, optionally, other therapeutic ingredients. The carrier(s) must be "pharmaceutically acceptable" in the sense of being compatible with the other ingredients of the formulation and not eliciting an unacceptable deleterious effect in the subject. Such carriers are described herein above or are otherwise well known to those skilled in the art of pharmacology. Desirably, the formulation should not include substances such as enzymes or oxidizing agents with which the biologically active agent to be administered is known to be incompatible. The formulations may be prepared by any of the methods well known in the art of pharmacy.

Within the compositions and methods of the invention, the PTH peptides, analogs and mimetics, and other biologically active agents disclosed herein may be administered to subjects by a variety of mucosal administration modes, including by oral, rectal, vaginal, intranasal, intrapulmonary, or transdermal delivery, or by topical delivery to the eyes, ears, skin or other mucosal surfaces. Optionally, PTH peptides, analogs and mimetics, and other biologically active agents disclosed herein can be coordinately or adjunctively administered by non-mucosal routes, including by intramuscular, subcutaneous, intravenous, intra-atrial, intra-articular, intraperitoneal, or parenteral routes. In other alternative embodiments, the biologically active agent(s) can be administered ex vivo by direct exposure to cells, tissues or organs originating from a mammalian subject, for example as a component of an ex vivo tissue or organ treatment formulation that contains the biologically active agent in a suitable, liquid or solid carrier.

Compositions according to the present invention are often administered in an aqueous solution as a nasal or pulmonary spray and may be dispensed in spray form by a variety of methods known to those skilled in the art. Preferred systems for dispensing liquids as a nasal spray are disclosed in U.S. Pat. No. 4,511,069, hereby incorporated by reference. The formulations may be presented in multi-dose containers, for example in the sealed dispensing system disclosed in U.S. Pat. No. 4,511,069. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Nasal and pulmonary spray solutions of the present invention typically comprise the drug or drug to be delivered, optionally formulated with a surface-active agent, such as a nonionic surfactant (e.g., polysorbate-80), and one or more buffers. In some embodiments of the present invention, the nasal spray solution further comprises a propellant. The pH of the nasal spray solution is optionally between about pH 3.0 and 6.0, preferably 5.0±0.3. Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, chlorobutanol, benzylalkonimum chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, mucosal formulations are administered as dry powder formulations comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5 µ mass median equivalent aerodynamic diameter (MMEAD), commonly about 1 µ MMEAD, and more typically about 2 µ MMEAD. Maximum particle size appropriate for deposition within the nasal passages is often about 10 μ MMEAD, commonly about 8 μ MMEAD, and more typically about 4 μ MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI), which rely on the patient's breath, upon pulmonary or nasal inhalation, to disperse the power into an aerosolized amount. Alternatively, the dry powder may be administered via air-assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the biologically active agent is lower than this amount, the powdered active agent will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

To formulate compositions for mucosal delivery within the present invention, the biologically active agent can be combined with various pharmaceutically acceptable additives, as well as a base or carrier for dispersion of the active agent(s). Desired additives include, but are not limited to, pH control agents, such as arginine, sodium hydroxide, glycine, hydrochloric acid, citric acid, etc. In addition, local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione) can be included. When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the nasal mucosa at the site of administration. Generally, the tonicity of the solution is adjusted to a value of about ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g. maleic anhydride) with other monomers (e.g. methyl (meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters, etc. can be employed as carriers. Hydrophilic polymers and other carriers can be used alone or in combination, and enhanced structural integrity can be imparted to the carrier by partial crystallization, ionic bonding, crosslinking and the like. The carrier can be provided in a variety of forms, including, fluid or viscous solutions, gels, pastes, powders, microspheres and films for direct application to the nasal mucosa. The use of a selected carrier in this context may result in promotion of absorption of the biologically active agent.

The biologically active agent can be combined with the base or carrier according to a variety of methods, and release of the active agent may be by diffusion, disintegration of the carrier, or associated formulation of water channels. In some circumstances, the active agent is dispersed in microcapsules (microspheres) or nanocapsules (nanospheres) prepared from a suitable polymer, e.g., isobutyl 2-cyanoacrylate and dispersed in a biocompatible dispersing medium applied to the nasal mucosa, which yields sustained delivery and biological activity over a protracted time.

To further enhance mucosal delivery of pharmaceutical agents within the invention, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compound include polyol compounds, such as oligo-, di- and monosaccharides such as sucrose, mannitol, sorbitol, lactose, L-arabinose, D-erythrose, D-ribose, D-xylose, D-mannose, trehalose, D-galactose, lactulose, cellobiose, gentibiose, glycerin and polyethylene glycol. Other examples of hydrophilic low molecular weight compounds useful as carriers within the invention include N-methylpyrrolidone, and alcohols (e.g. oligovinyl alcohol, ethanol, ethylene glycol, propylene glycol, etc.) These hydrophilic low molecular weight compounds can be used alone or in combination with one another or with other active or inactive components of the intranasal formulation.

The compositions of the invention may alternatively contain as pharmaceutically acceptable carriers substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

Therapeutic compositions for administering the biologically active agent can also be formulated as a solution, microemulsion, or other ordered structure suitable for high concentration of active ingredients. The carrier can be a solvent or dispersion medium containing, for example, water, ethanol, polyol (for example, glycerol, propylene glycol, and liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols such as mannitol, sorbitol, or sodium chloride in the composition. Prolonged absorption of the biologically active agent can be brought about by including in the composition an agent which delays absorption, for example, monostearate salts and gelatin.

In certain embodiments of the invention, the biologically active agent is administered in a time-release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the invention can be brought about by including in the composition agents that delay absorption, for example, aluminum monosterate hydrogels and gelatin. When controlled release formulations of the biologically active agent is desired, controlled release binders suitable for use in accordance with the invention include any biocompatible controlled-release material which is inert to the active agent and which is capable of incorporating the biologically active agent. Numerous such materials are known in the art. Useful controlled-release binders are materials that are metabolized slowly under physiological conditions following their intranasal delivery (e.g., at the nasal mucosal surface, or in the presence of bodily fluids following transmucosal delivery). Appropriate binders include but are not limited to biocompatible polymers and copolymers previously used in the art in sustained release formulations. Such biocompatible compounds are non-toxic and inert to surrounding tissues, and do not trigger significant adverse side effects such as nasal irritation, immune response, inflammation, or the like. They are metabolized into metabolic products that are also biocompatible and easily eliminated from the body.

Exemplary polymeric materials for use in this context include, but are not limited to, polymeric matrices derived from copolymeric and homopolymeric polyesters having hydrolysable ester linkages. A number of these are known in the art to be biodegradable and to lead to degradation products having no or low toxicity. Exemplary polymers include polyglycolic acids (PGA) and polylactic acids (PLA), poly(DL-lactic acid-co-glycolic acid)(DL PLGA), poly(D-lactic acid-coglycolic acid)(D PLGA) and poly(L-lactic acid-co-glycolic acid)(L PLGA). Other useful biodegradable or bioerodable polymers include but are not limited to such polymers as poly(epsilon-caprolactone), poly(epsilon-aprolactone-CO-lactic acid), poly(E-aprolactone-CO-glycolic acid), poly(beta-hydroxy butyric acid), poly(alkyl-2-cyanoacrilate), hydrogels such as poly(hydroxyethyl methacrylate), polyamides, poly(amino acids) (i.e., L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof. Many methods for preparing such formulations are generally known to those skilled in the art. Other useful formulations include controlled-release compositions e.g., microcapsules, U.S. Pat. Nos. 4,652,441 and 4,917,893, lactic acid-glycolic acid copolymers useful in making microcapsules and other formulations, U.S. Pat. Nos. 4,677,191 and 4,728,721, and sustained-release compositions for water-soluble peptides, U.S. Pat. No. 4,675,189, all patents hereby incorporated by reference.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders, methods of preparation include vacuum drying and freeze-drying which yields a powder of the active ingredient plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Mucosal administration according to the invention allows effective self-administration of treatment by patients, provided that sufficient safeguards are in place to control and monitor dosing and side effects. Mucosal administration also overcomes certain drawbacks of other administration forms, such as injections, that are painful and expose the patient to possible infections and may present drug bioavailability problems. For nasal and pulmonary delivery, systems for controlled aerosol dispensing of therapeutic liquids as a spray are well known. In one embodiment, metered doses of active agent are delivered by means of a specially constructed mechanical pump valve, U.S. Pat. No. 4,511,069.

For prophylactic and treatment purposes, the biologically active agent(s) disclosed herein may be administered to the subject intranasally once daily. In this context, a therapeutically effective dosage of the PTH peptide may include repeated doses within a prolonged prophylaxis or treatment regimen that will yield clinically significant results to alleviate or prevent osteoporosis or osteopenia. Determination of effective dosages in this context is typically based on animal model studies followed up by human clinical trials and is guided by determining effective dosages and administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

The actual dosage of biologically active agents will of course vary according to factors such as the disease indication and particular status of the subject (e.g., the subject's age, size, fitness, extent of symptoms, susceptibility factors, etc), time and route of administration, other drugs or treatments being administered concurrently, as well as the specific pharmacology of the biologically active agent(s) for eliciting the desired activity or biological response in the subject. Dosage regimens may be adjusted to provide an optimum prophylactic or therapeutic response. A therapeutically effective amount is also one in which any toxic or detrimental side effects of the biologically active agent are outweighed in clinical terms by therapeutically beneficial effects. A non-limiting range for a therapeutically effective amount of a PTH peptide within the methods and formulations of the invention is 0.7 µg/kg to about 25 µg/kg. To treat osteoporosis or osteopenia, an intranasal dose of PTH peptide is administered at dose high enough to promote the increase in bone mass but low enough so as not to induce any unwanted side-effects such as nausea. A preferred intranasal dose of parathyroid hormone$_{1-34}$ is about 1 µg-10 µg/kg weight of the patient, most preferably from about 1.5 µg/kg to about 3 µg/kg weight of the patient. In a standard dose a patient will receive 50 µg to 1600 µg, more preferably about between 75 µg to 800 µg, most preferably 100 µg, 150 µg, 200 µg to about 400 µg. Alternatively, a non-limiting range for a therapeutically effective amount of a biologically active agent within the methods and formulations of the invention is between about 0.001 pmol to about 100 pmol per kg body weight, between about 0.01 pmol to about 10 pmol per kg body weight, between about 0.1 pmol to about 5 pmol per kg body weight, or between about 0.5 pmol to about 1.0 pmol per kg body weight. Per administration, it is desirable to administer at least one microgram of the biologically active agent (e.g., one or more PTH peptide proteins, analogs and mimetics, and other biologically active agents), more typically between about 10 µg and 5.0 mg, and in certain embodiments between about 100 µg and 1.0 or 2.0 mg to an average human subject. For certain oral applications, doses as high as 0.5 mg per kg body weight may be necessary to achieve adequate plasma levels. It is to be further noted that for each particular subject, specific dosage regimens should be evaluated and adjusted over time according to the individual need and professional judgment of the person administering or supervising the administration of the permeabilizing peptide(s) and other biologically active agent(s). An intranasal dose of a parathyroid hormone will range from 50 µg to 1600 µg of parathyroid hormone, preferably 75 µg to 800 µg, more preferably 100 µg to 400 µg with a most preferred dose being between 100 µg to 200 µg with 150 µg being a dose that is considered to be highly effective. Repeated intranasal dosing with the formulations of the invention, on a schedule ranging from about 0.1 to 24 hours between doses, preferably between 0.5 and 24.0 hours between doses, will maintain normalized, sustained therapeutic levels of PTH peptide to maximize clinical benefits while minimizing the risks of excessive exposure and side effects. The goal is to mucosally deliver an amount of the PTH peptide sufficient to raise the concentration of the PTH peptide in the plasma of an individual to promote increase in bone mass.

Dosage of PTH agonists such as parathyroid hormone may be varied by the attending clinician or patient, if self administering an over the counter dosage form, to maintain a desired concentration at the target site.

In an alternative embodiment, the invention provides compositions and methods for intranasal delivery of PTH peptide, wherein the PTH peptide compound(s) is/are repeatedly administered through an intranasal effective dosage regimen that involves multiple administrations of the PTH peptide to the subject during a daily or weekly schedule to maintain a therapeutically effective elevated and lowered pulsatile level of PTH peptide during an extended dosing period. The compositions and method provide PTH peptide compound(s) that are self-administered by the subject in a nasal formulation between one and six times daily to maintain a therapeutically effective elevated and lowered pulsatile level of PTH peptide during an 8 hour to 24 hour extended dosing period.

The instant invention also includes kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains one or more PTH peptide proteins, analogs or mimetics, and/or other biologically active agents in combination with mucosal delivery enhancing agents disclosed herein formulated in a pharmaceutical preparation for mucosal delivery.

The intranasal formulations of the present invention can be administered using any spray bottle or syringe. An example of a nasal spray bottle is the, "Nasal Spray Pump w/Safety Clip", Pfeiffer SAP # 60548, which delivers a dose of 0.1 mL per squirt and has a diptube length of 36.05 mm. It can be purchased from Pfeiffer of America of Princeton, N.J. Intranasal doses of a PTH peptide such as parathyroid hormone can range from 0.1 µg/kg to about 1500 µg/kg. When administered in as an intranasal spray, it is preferable that the particle size of the spray is between 10-100 µm (microns) in size, preferably 20-100 µm in size.

We have discovered that the parathyroid hormone peptides can be administered intranasally using a nasal spray or aerosol. This is surprising because many proteins and peptides have been shown to be sheared or denatured due to the mechanical forces generated by the actuator in producing the spray or aerosol. In this area the following definitions are useful.

1. Aerosol—A product that is packaged under pressure and contains therapeutically active ingredients that are released upon activation of an appropriate valve system.
2. Metered aerosol—A pressurized dosage form comprised of metered dose valves, which allow for the delivery of a uniform quantity of spray upon each activation.
3. Powder aerosol—A product that is packaged under pressure and contains therapeutically active ingredients in the form of a powder, which are released upon activation of an appropriate valve system.
4. Spray aerosol—An aerosol product that utilizes a compressed gas as the propellant to provide the force necessary to expet the product as a wet spray; it generally applicable to solutions of medicinal agents in aqueous solvents.
5. Spray—A liquid minutely divided as by a jet of air or steam. Nasal spray drugproducts contain therapeutically active ingredients dissolved or suspended in solutions or mixtures of excipients in nonpressurized dispensers.
6. Metered spray—A non-pressurized dosage form consisting of valves that allow the dispensing of a specified quantity of spray upon each activation.
7. Suspension spray—A liquid preparation containing solid particles dispersed in a liquid vehicle and in the form of course droplets or as finely divided solids.

The fluid dynamic characterization of the aerosol spray emitted by metered nasal spray pumps as a drug delivery device ("DDD"). Spray characterization is an integral part of the regulatory submissions necessary for Food and Drug Administration ("FDA") approval of research and development, quality assurance and stability testing procedures for new and existing nasal spray pumps.

Thorough characterization of the spray's geometry has been found to be the best indicator of the overall performance of nasal spray pumps. In particular, measurements of the spray's divergence angle (plume geometry) as it exits the device; the spray's cross-sectional ellipticity, uniformity and particle/droplet distribution (spray pattern); and the time evolution of the developing spray have been found to be the most representative performance quantities in the characterization of a nasal spray pump. During quality assurance and stability testing, plume geometry and spray pattern measurements are key identifiers for verifying consistency and conformity with the approved data criteria for the nasal spray pumps.

Definitions

Plume Height—the measurement from the actuator tip to the point at which the plume angle becomes non-linear because of the breakdown of linear flow. Based on a visual examination of digital images, and to establish a measurement point for width that is consistent with the farthest measurement point of spray pattern, a height of 30 mm is defined for this study Major Axis—the largest chord that can be drawn within the fitted spray pattern that crosses the COMw in base units (mm)

Minor Axis—the smallest chord that can be drawn within the fitted spray pattern that crosses the COMw in base units (mm)

Ellipticity Ratio—the ratio of the major axis to the minor axis $D_{10}$—the diameter of droplet for which 10% of the total liquid volume of sample consists of droplets of a smaller diameter (μm)

$D_{50}$—the diameter of droplet for which 50% of the total liquid volume of sample consists of droplets of a smaller diameter (μm), also known as the mass median diameter $D_{90}$—the diameter of droplet for which 90% of the total liquid volume of sample consists of droplets of a smaller diameter (μm)

Span—measurement of the width of the distribution, The smaller the value, the narrower the distribution. Span is calculated as $$\frac{(D_{90} - D_{10})}{D_{50}}.$$

% RSD—percent relative standard deviation, the standard deviation divided by the mean of the series and multiplied by 100, also known as % CV.

A nasal spray device can be selected according to what is customary in the industry or acceptable by the regulatory health authorities. One example of a suitable device is described in described in U.S. application Ser. No. 10/869,649 (S. Quay and G. Brandt: Compositions and methods for enhanced mucosal delivery of Y2 receptor-binding peptides and methods for treating and preventing obesity, filed Jun. 16, 2004).

To treat osteoporosis or osteopenia, an intranasal dose of a PTH peptide parathyroid hormone is administered at dose high enough to promote an increase in bone mass but low enough so as not to induce any unwanted side-effects such as nausea A preferred intranasal dose of a PTH peptide such as parathyroid hormone(1-34) is about 3 μg-10 μg/kg weight of the patient, most preferably about 6 μg/kg weight of the patient. In a standard dose a patient will receive 50 μg to 800 μg, more preferably about between 100 μg to 400 μg, most preferably 150 μg to about 200 μg. The a PTH peptide such as parathyroid hormone (1-34) is preferably administered once a day.

The following examples are provided by way of illustration, not limitation.

EXAMPLE 1

An exemplary formulation for enhanced nasal mucosal delivery of PTH following the teachings of the instant specification can be prepared and evaluated as shown in Table 1.

EXAMPLE 2

Nasal Mucosal Delivery—Permeation Kinetics and Cytotoxicity

The following methods are generally useful for evaluating nasal mucosal delivery parameters, kinetics and side effects for PTH within the formulations and method of the invention, as well as for determining the efficacy and characteristics of the various intranasal delivery-enhancing agents disclosed herein for combinatorial formulation or coordinate administration with PTH.

Permeation kinetics and cytotoxicity are also useful for determining the efficacy and characteristics of the various mucosal delivery-enhancing agents disclosed herein for combinatorial formulation or coordinate administration with mucosal delivery-enhancing agents. In one exemplary protocol, permeation kinetics and lack of unacceptable cytotoxicity are demonstrated for an intranasal delivery-enhancing agent as disclosed above in combination with a biologically active therapeutic agent, exemplified by PTH.

The EPIAIRWAY® system was developed by MatTek Corp (Ashland, Mass.) as a model of the pseudostratified epithelium lining the respiratory tract. The epithelial cells are grown on porous membrane-bottomed cell culture inserts at an air-liquid interface, which results in differentiation of the cells to a highly polarized morphology. The apical surface is ciliated with a microvillous ultrastructure and the epithelium produces mucus (the presence of mucin has been confirmed by immunoblotting). The inserts have a diameter of 0.875 cm, providing a surface area of 0.6 cm². The cells are plated onto the inserts at the factory approximately three weeks before shipping.

On arrival, the units are placed onto sterile supports in 6-well microplates. Each well receives 5 mL of proprietary culture medium. This DMEM-based medium is serum free but is supplemented with epidermal growth factor and other factors. The medium is always tested for endogenous levels of any cytokine or growth factor, which is being considered for intranasal delivery, but has been free of all cytokines and factors studied to date except insulin. The 5 mL volume is just sufficient to provide contact to the bottoms of the units on their stands, but the apical surface of the epithelium is allowed to remain in direct contact with air. Sterile tweezers are used in this step and in all subsequent steps involving transfer of units to liquid-containing wells to ensure that no air is trapped between the bottoms of the units and the medium.

The units in their plates are maintained at 37° C. in an incubator in an atmosphere of 5% $CO_2$ in air for 24 hours. At the end of this time the medium is replaced with fresh medium and the units are returned to the incubator for another 24 hours.

A "kit" of 24 EPIAIRWAY® units can routinely be employed for evaluating five different formulations, each of which is applied to quadruplicate wells. Each well is employed for determination of permeation kinetics (4 time points), transepithelial resistance, mitochondrial reductase activity as measured by MTT reduction, and cytolysis as measured by release of LDH. An additional set of wells is employed as controls, which are sham treated during determination of permeation kinetics, but are otherwise handled identically to the test sample-containing units for determinations of transepithelial resistance and viability. The determinations on the controls are routinely also made on quadruplicate units, but occasionally we have employed triplicate units for the controls and have dedicated the remaining four units in the kit to measurements of transepithelial resistance and viability on untreated units or we have frozen and thawed the units for determinations of total LDH levels to serve as a reference for 100% cytolysis.

In all experiments, the nasal mucosal delivery formulation to be studied is applied to the apical surface of each unit in a volume of 100 µL, which is sufficient to cover the entire apical surface. An appropriate volume of the test formulation at the concentration applied to the apical surface (no more than 100 µL is generally needed) is set aside for subsequent determination of concentration of the active material by ELISA or other designated assay.

The units are placed in 6 well plates without stands for the experiment: each well contains 0.9 mL of medium which is sufficient to contact the porous membrane bottom of the unit but does not generate any significant upward hydrostatic pressure on the unit.

To minimize potential sources of error and avoid any formation of concentration gradients, the units are transferred from one 0.9 mL-containing well to another at each time point in the study. These transfers are made at the following time points, based on a zero time at which the 100 µL volume of test material was applied to the apical surface: 15 minutes, 30 minutes, 60 minutes, and 120 minutes.

In between time points the units in their plates are kept in the 37° C. incubator. Plates containing 0.9 mL medium per well are also maintained in the incubator so that minimal change in temperature occurs during the brief periods when the plates are removed and the units are transferred from one well to another using sterile forceps.

At the completion of each time point, the medium is removed from the well from which each unit was transferred, and aliquotted into two tubes (one tube receives 700 µL and the other 200 µL) for determination of the concentration of permeated test material and, in the event that the test material is cytotoxic, for release of the cytosolic enzyme, lactic dehydrogenase, from the epithelium. These samples are kept in the refrigerator if the assays are to be conducted within 24 hours, or the samples are subaliquotted and kept frozen at −80° C. until thawed once for assays. Repeated freeze-thaw cycles are to be avoided.

In order to minimize errors, all tubes, plates, and wells are prelabeled before initiating an experiment.

At the end of the 120 minute time point, the units are transferred from the last of the 0.9 mL containing wells to 24-well microplates, containing 0.3 mL medium per well. This volume is again sufficient to contact the bottoms of the units, but not to exert upward hydrostatic pressure on the units. The units are returned to the incubator prior to measurement of transepithelial resistance.

Respiratory airway epithelial cells form tight junctions in vivo as well as in vitro, restricting the flow of solutes across the tissue. These junctions confer a transepithelial resistance of several hundred ohms×cm$^2$ in excised airway tissues; in the MatTek EPIAIRWAY® units, the transepithelial resistance (TER) is claimed by the manufacturer to be routinely around 1000 ohms×cm$^2$. We have found that the TER of control EPIAIRWAY® units which have been sham-exposed during the sequence of steps in the permeation study is somewhat lower (700-800 ohms×cm$^2$), but, since permeation of small molecules is proportional to the inverse of the TER, this value is still sufficiently high to provide a major barrier to permeation. The porous membrane-bottomed units without cells, conversely, provide only minimal transmembrane resistance (5-20 ohms×cm$^2$).

Accurate determinations of TER require that the electrodes of the ohmmeter be positioned over a significant surface area above and below the membrane, and that the distance of the electrodes from the membrane be reproducibly controlled. The method for TER determination recommended by MatTek and employed for all experiments here employs an "EVOM"™ epithelial voltohmmeter and an "ENDOHM"™ tissue resistance measurement chamber from World Precision Instruments, Inc., Sarasota, Fla.

The chamber is initially filled with Dulbecco's phosphate buffered saline (PBS) for at least 20 minutes prior to TER determinations in order to equilibrate the electrodes.

Determinations of TER are made with 1.5 mL of PBS in the chamber and 350 µL of PBS in the membrane-bottomed unit being measured. The top electrode is adjusted to a position just above the membrane of a unit containing no cells (but containing 350 µL of PBS) and then fixed to ensure reproducible positioning. The resistance of a cell-free unit is typically 5-20 ohms×cm$^2$ ("background resistance").

Once the chamber is prepared and the background resistance is recorded, units in a 24-well plate which had just been employed in permeation determinations are removed from the incubator and individually placed in the chamber for TER determinations.

Each unit is first transferred to a petri dish containing PBS to ensure that the membrane bottom is moistened. An aliquot of 350 µL PBS is added to the unit and then carefully aspirated into a labeled tube to rinse the apical surface. A second wash of 350 µL PBS is then applied to the unit and aspirated into the same collection tube.

The unit is blotted free of excess PBS on its exterior surface only before being placed into the chamber (containing a fresh 1.5 mL aliquot of PBS). An aliquot of 350 µL PBS is added to the unit before the top electrode is placed on the chamber and the TER is read on the EVOM meter.

After the TER of the unit is read in the ENDOHM chamber, the unit is removed, the PBS is aspirated and saved, and the unit is returned with an air interface on the apical surface to a 24-well plate containing 0.3 mL medium per well.

The units are read in the following sequence: all sham-treated controls, followed by all formulation-treated samples, followed by a second TER reading of each of the sham-treated controls. After all the TER determinations are complete, the units in the 24-well microplate are returned to the incubator for determination of viability by MTT reduction.

MTT is a cell-permeable tetrazolium salt which is reduced by mitochondrial dehydrogenase activity to an insoluble colored formazan by viable cells with intact mitochondrial function or by nonmitochondrial NAD(P)H dehydrogenase activity from cells capable of generating a respiratory burst formation of formazan is a good indicator of viability of epithelial cells since these cells do not generate a significant respiratory burst. We have employed a MTT reagent kit prepared by MatTek Corp for their units in order to assess viability.

The MTT reagent is supplied as a concentrate and is diluted into a proprietary DMEM-based diluent on the day viability is to be assayed (typically the afternoon of the day in which permeation kinetics and TER were determined in the morning). Insoluble reagent is removed by a brief centrifugation before use. The final MTT concentration is 1 mg/mL.

The final MTT solution is added to wells of a 24-well microplate at a volume of 300 μL per well. As has been noted above, this volume is sufficient to contact the membranes of the EPIAIRWAY® units but imposes no significant positive hydrostatic pressure on the cells. The units are removed from the 24-well plate in which they were placed after TER measurements, and after removing any excess liquid from the exterior surface of the units, they are transferred to the plate containing MTT reagent. The units in the plate are then placed in an incubator at 37° C. in an atmosphere of 5% $CO_2$ in air for 3 hours.

At the end of the 3-hour incubation, the units containing viable cells will have turned visibly purple. The insoluble formazan must be extracted from the cells in their units to quantitate the extent of MTT reduction. Extraction of the formazan is accomplished by transferring the units to a 24-well microplate containing 2 mL extractant solution per well, after removing excess liquid from the exterior surface of the units as before. This volume is sufficient to completely cover both the membrane and the apical surface of the units. Extraction is allowed to proceed overnight at room temperature in a light-tight chamber. MTT extractants traditionally contain high concentrations of detergent, and destroy the cells.

At the end of the extraction, the fluid from within each unit and the fluid in its surrounding well are combined and transferred to a tube for subsequent aliquotting into a 96-well microplate (200 μL aliquots are optimal) and determination of absorbance at 570 nm on a VMax multiwell microplate spectrophotometer. To ensure that turbidity from debris coming from the extracted units does not contribute to the absorbance, the absorbance at 650 nm is also determined for each well in the VMax and is automatically subtracted from the absorbance at 570 nm. The "blank" for the determination of formazan absorbance is a 200 μL aliquot of extractant to which no unit had been exposed. This absorbance value is assumed to constitute zero viability.

Two units from each kit of 24 EPIAIRWAY® units are left untreated during determination of permeation kinetics and TER. These units are employed as the positive control for 100% cell viability. In all the studies we have conducted, there has been no statistically significant difference in the viability of the cells in these untreated units vs cells in control units which had been sham treated for permeation kinetics and on which TER determinations had been performed. The absorbance of all units treated with test formulations is assumed to be linearly proportional to the percent viability of the cells in the units at the time of the incubation with MTT. It should be noted that this assay is carried out typically no sooner than four hours after introduction of the test material to the apical surface, and subsequent to rinsing of the apical surface of the units during TER determination.

While measurement of mitochondrial reductase activity by MTT reduction is a sensitive probe of cell viability, the assay necessarily destroys the cells and therefore can be carried out only at the end of each study. When cells undergo necrotic lysis, their cytotosolic contents are spilled into the surrounding medium, and cytosolic enzymes such as lactic dehydrogenase (LDH) can be detected in this medium. An assay for LDH in the medium can be performed on samples of medium removed at each time point of the two-hour determination of permeation kinetics. Thus, cytotoxic effects of formulations which do not develop until significant time has passed can be detected as well as effects of formulations which induce cytolysis with the first few minutes of exposure to airway epithelium.

The recommended LDH assay for evaluating cytolysis of the EPIAIRWAY® units is based on conversion of lactate to pyruvate with generation of NADH from NAD. The NADH is then reoxidized along with simultaneous reduction of the tetrazolium salt INT, catalyzed by a crude "diaphorase" preparation. The formazan formed from reduction of INT is soluble, so that the entire assay for LDH activity can be carried out in a homogenous aqueous medium containing lactate, NAD, diaphorase, and INT.

The assay for LDH activity is carried out on 50 μL aliquots from samples of "supernatant" medium surrounding an EPIAIRWAY® unit and collected at each time point. These samples were either stored for no longer than 24 h in the refrigerator or were thawed after being frozen within a few hours after collection. Each EPIAIRWAY® unit generates samples of supernatant medium collected at 15 min, 30 min, 1 h, and 2 h after application of the test material. The aliquots are all transferred to a 96 well microplate.

A 50 μL aliquot of medium which had not been exposed to a unit serves as a "blank" or negative control of 0% cytotoxicity. We have found that the apparent level of "endogenous" LDH present after reaction of the assay reagent mixture with the unexposed medium is the same within experimental error as the apparent level of LDH released by all the sham-treated control units over the entire time course of 2 hours required to conduct a permeation kinetics study. Thus, within experimental error, these sham-treated units show no cytolysis of the epithelial cells over the time course of the permeation kinetics measurements.

To prepare a sample of supernatant medium reflecting the level of LDH released after 100% of the cells in a unit have lysed, a unit which had not been subjected to any prior manipulations is added to a well of a 6-well microplate containing 0.9 mL of medium as in the protocol for determination of permeation kinetics, the plate containing the unit is frozen at −80° C., and the contents of the well are then allowed to thaw. This freeze-thaw cycle effectively lyses the cells and releases their cytosolic contents, including LDH, into the supernatant medium. A 50 μL aliquot of the medium from the frozen and thawed cells is added to the 96-well plate as a positive control reflecting 100% cytotoxicity.

To each well containing an aliquot of supernatant medium, a 50 μL aliquot of the LDH assay reagent is added. The plate is then incubated for 30 minutes in the dark.

The reactions are terminated by addition of a "stop" solution of 1 M acetic acid, and within one hour of addition of the stop solution, the absorbance of the plate is determined at 490 nm.

Computation of percent cytolysis is based on the assumption of a linear relationship between absorbance and cytolysis, with the absorbance obtained from the medium alone serving as a reference for 0% cytolysis and the absorbance obtained from the medium surrounding a frozen and thawed unit serving as a reference for 100% cytolysis.

The procedures for determining the concentrations of biologically active agents as test materials for evaluating enhanced permeation of active agents in conjunction with coordinate administration of mucosal delivery-enhancing agents or combinatorial formulation of the invention are generally as described above and in accordance with known methods and specific manufacturer instructions of ELISA kits employed for each particular assay. Permeation kinetics of the biologically active agent is generally determined by taking measurements at multiple time points (for example 15 min., 30 min., 60 min. and 120 min) after the biologically active agent is contacted with the apical epithelial cell surface (which may be simultaneous with, or subsequent to, exposure of the apical cell surface to the mucosal delivery-enhancing agent(s)).

The procedures for determining the concentrations of PTH peptide in blood serum, central nervous system (CNS) tissues or fluids, cerebral spinal fluid (CSF), or other tissues or fluids of a mammalian subject may be determined by immunologic assay for PTH. The procedures for determining the concentrations of PTH as test materials for evaluating enhanced permeation of active agents in conjunction with coordinate administration of mucosal delivery-enhancing agents or combinatorial formulation of the invention are generally as described above and in accordance with known methods and specific manufacturer instructions for radioimmunoassay (RIA), enzyme immunoassay (EIA), and antibody reagents for immunohistochemistry or immunofluorescence for PTH peptide. Bachem AG (King of Prussia, Pa.).

EPIAIRWAY® tissue membranes are cultured in phenol red and hydrocortisone free medium (MatTek Corp., Ashland, Mass.). The tissue membranes are cultured at 37° C. for 48 hours to allow the tissues to equilibrate. Each tissue membrane is placed in an individual well of a 6-well plate containing 0.9 mL of serum free medium. 100 µL of the formulation (test sample or control) is applied to the apical surface of the membrane. Triplicate or quadruplicate samples of each test sample (mucosal delivery-enhancing agent in combination with a biologically active agent, PTH) and control (biologically active agent, PTH, alone) are evaluated in each assay. At each time point (15, 30, 60 and 120 minutes) the tissue membranes are moved to new wells containing fresh medium. The underlying 0.9 mL medium samples is harvested at each time point and stored at 4° C. for use in ELISA and lactate dehydrogenase (LDH) assays.

The ELISA kits are typically two-step sandwich ELISAs: the immunoreactive form of the agent being studied is first "captured" by an antibody immobilized on a 96-well microplate and after washing unbound material out of the wells, a "detection" antibody is allowed to react with the bound immunoreactive agent. This detection antibody is typically conjugated to an enzyme (most often horseradish peroxidase) and the amount of enzyme bound to the plate in immune complexes is then measured by assaying its activity with a chromogenic reagent. In addition to samples of supernatant medium collected at each of the time points in the permeation kinetics studies, appropriately diluted samples of the formulation (i.e., containing the subject biologically active test agent) that was applied to the apical surface of the units at the start of the kinetics study are also assayed in the ELISA plate, along with a set of manufacturer-provided standards. Each supernatant medium sample is generally assayed in duplicate wells by ELISA (it will be recalled that quadruplicate units are employed for each formulation in a permeation kinetics determination, generating a total of sixteen samples of supernatant medium collected over all four time points).

It is not uncommon for the apparent concentrations of active test agent in samples of supernatant medium or in diluted samples of material applied to the apical surface of the units to lie outside the range of concentrations of the standards after completion of an ELISA. No concentrations of material present in experimental samples are determined by extrapolation beyond the concentrations of the standards; rather, samples are rediluted appropriately to generate concentrations of the test material which can be more accurately determined by interpolation between the standards in a repeat ELISA.

The ELISA for a biologically active test agent, for example, PTH, is unique in its design and recommended protocol. Unlike most kits, the ELISA employs two monoclonal antibodies, one for capture and another, directed towards a nonoverlapping determinant for the biologically active test agent, e.g., PTH, as the detection antibody (this antibody is conjugated to horseradish peroxidase). As long as concentrations of PTH that lie below the upper limit of the assay are present in experimental samples, the assay protocol can be employed as per the manufacturer's instructions, which allow for incubation of the samples on the ELISA plate with both antibodies present simultaneously. When the PTH levels in a sample are significantly higher than this upper limit, the levels of immunoreactive PTH may exceed the amounts of the antibodies in the incubation mixture, and some PTH which has no detection antibody bound will be captured on the plate, while some PTH which has detection antibody bound may not be captured. This leads to serious underestimation of the PTH levels in the sample (it will appear that the PTH levels in such a sample lie significantly below the upper limit of the assay). To eliminate this possibility, the assay protocol has been modified:

The diluted samples are first incubated on the ELISA plate containing the immobilized capture antibody for one hour in the absence of any detection antibody. After the one hour incubation, the wells are washed free of unbound material.

The detection antibody is incubated with the plate for one hour to permit formation of immune complexes with all captured antigen. The concentration of detection antibody is sufficient to react with the maximum level of PTH which has been bound by the capture antibody. The plate is then washed again to remove any unbound detection antibody.

The peroxidase substrate is added to the plate and incubated for fifteen minutes to allow color development to take place.

The "stop" solution is added to the plate, and the absorbance is read at 450 nm as well as 490 nm in the VMax microplate spectrophotometer. The absorbance of the colored product at 490 nm is much lower than that at 450 nm, but the absorbance at each wavelength is still proportional to concentration of product. The two readings ensure that the absorbance is linearly related to the amount of bound PTH over the working range of the VMax instrument (we routinely restrict the range from 0 to 2.5 OD, although the instrument is reported to be accurate over a range from 0 to 3.0 OD). The amount of PTH in the samples is determined by interpolation between the OD values obtained for the different standards included in the ELISA. Samples with OD readings outside the range obtained for the standards are rediluted and run in a repeat ELISA.

Measurement of transepithelial resistance by TER Assay:

After the final assay time points, membranes are placed in individual wells of a 24 well culture plate in 0.3 mL of clean medium and the trans epithelial electrical resistance (TER) is measured using the EVOM Epithelial Voltohmmeter and an Endohm chamber (World Precision Instruments, Sarasota, Fla.). The top electrode is adjusted to be close to, but not in contact with, the top surface of the membrane. Tissues are removed, one at a time, from their respective wells and basal surfaces are rinsed by dipping in clean PBS. Apical surfaces were gently rinsed twice with PBS. The tissue unit is placed in the Endohm chamber, 250 µL of PBS added to the insert, the top electrode replaced and the resistance measured and recorded. Following measurement, the PBS is decanted and the tissue insert is returned to the culture plate. All TER values are reported as a function of the surface area of the tissue.

The final numbers are calculated as:

TER of cell membrane=(Resistance ($R$) of Insert with membrane–$R$ of blank Insert)×Area of membrane (0.6 cm$^2$).

EXAMPLE 3

Preparation of a Parathyroid Hormone Formulation Free of a Stabilizer that is a Protein A parathyroid hormone formulation suitable for intranasal administration of parathyroid hormone, which was substantially free of a stabilizer that is a protein was prepared having the formulation listed below. About ¾ of the water was added to a beaker and stirred with a stir bar on a stir plate and the sodium citrate was added until it was completely dissolved. The EDTA was then added and stirred until it was completely dissolved. The citric acid was then added and stirred until it was completely dissolved. The methyl-β-cyclodextrin was added and stirred until it was completely dissolved. The DDPC was then added and stirred until it was completely dissolved. The lactose was then added and stirred until it was completely dissolved. The sorbitol was then added and stirred until it was completely dissolved. The chlorobutanol was then added and stirred until it was completely dissolved. The parathyroid hormone 1-34 was added and stirred gently until it dissolved. The pH was adjuste to 5.0±0.25 by addition of HCl or NaOH. Water was added to final volume.

EXAMPLE 4

PTH and Enhancer Effects on Human Chondrocytes

The effect of intranasal PTH$_{1-34}$ formulation on human chondrocytes was measured in vitro, specifically measuring the effect of permeation enhancers on chondrocyte proliferation and production of collagen in comparison to calcitonin and IGF-1.

The cell lines used were derived from human articular cartilage. Articular chondrocytes are phenotypically very similar to nasal chondrocytes (Shikani et al., 2004), and thus provided a good model for the current study. The cells were provided in two different forms, the first as a monolayer (proliferation model) and the second as cells encapsulated in alginate beads (redifferention model).

The cell monolayer model was employed to examine cell proliferation. The objective was to examine cell proliferation in the presence of PTH$_{1-34}$ in a simple formulation (citrate buffer) or a formulation containing formulation enhancers, and then compare these data to cell proliferation for a positive control (media containing antibiotics, insulin, TGF-beta and IGF-1) and negative control (media devoid of any cell growth components). A placebo solution used to make peptide-containing formulations is described in Table 3. Peptide was added to this solution to achieve the desired concentration. PTH$_{1-34}$ and salmon calcitonin used were from Nastech. IGF-1 was purchased from Sigma.

Chondrocyte monolayers (Cell Applications, Inc., San Diego, Calif.) derived from normal human cartilage were adhered on to a 24-well plate and shipped following the first doubling. Approximately 16000 cells per well were expected at the time the cells were received. Two plates were treated identically with PTH$_{1-34}$ and appropriate control samples. Controls included cells treated with chondrocyte growth media for positive control (Cell Applications) and cells treated with basal media for negative control (Cell Applications). Once treated, one of the two plates was analyzed for cell viability (t=0 sample). The second plate was placed at 37° C., 5% $CO_2$ incubator for 4 days, after which the plates were analyzed using the MTT assay.

For MTT analysis (Cell Applications), a volume of 100 µL MTT concentrate solution was added to each well containing 1000 µL sample. Plates were sealed and placed at 37° C. for 4 hours. Each plate was removed from 37° C. after 4 h incubation and placed on a bench top. Supernatant from each well was carefully removed and discarded. Visible purple crystals were seen attached to the bottom of the plated in each well. A volume of 500 µL of extraction solution was then added into each well. Plates were sealed with parafilm immediately after adding extraction solution, and then gently rocked and/or swirled to solubilize the purple crystals. Absorbance was read at 570 nm.

Approximately 3 million human chondrocyte cells (Cell Applications) encapsulated in alginate beads were received in 25 mL total volume of re-differentiated medium. Human chondrocytes in alginate beads produce their phenotypic markers such as aggrecan and Type II collagen (Benya et al., 1982; Guo et al., 1982; Kato et al., 1984) unlike in monolayer culture where chondrocytes lose their phenotypic characteristics and de-differentiate to fibroblast-like cells (Kuettmer et al., 1982; Jennings et al., 1983; Kato et al., 1984). Alginate based cell system was pursued to assess Type H collagen expression as result of PTH$_{1-34}$ dosing and therefore indication of any cartilage growth.

The cell-containing alginate bead suspension was transferred from cell culture flask to 50 mL conical tubes. A volume of 500 µL (~62,500 cells per well) suspension was dispensed per well in 24-well plates. Samples were added to each well and final volume was brought to one milliliter with appropriate growth media. Controls included cells treated with re-differentiated media as positive control (Cell Applications), cells treated with chondrocyte growth media (Cell Applications) and basal media (Cell Applications) as negative controls.

Plates were swirled gently to allow homogenous mixture of each sample. Plates were placed in 37° C., 5% $CO_2$ incubator. Human chondrocytes were grown for up to 12 days on longer. Appropriate growth media were replaced every second or third day. Alginate beads were prepared for Type II collagen extraction on the last day of the experiment and extracted collagen was quantitated using Native Type II Collagen Detection Kit (Chondrex Inc., Redmond Wash.). A capture ELISA kit (Chondrex) was used to measure native type II collagen. Glycosaminoglycans were measured by a kit (Accurate Chemical & Scientific Corp).

The MTT assay was employed to test for cell proliferation. The MTT assay measures cell viability, and an increase or decrease in the MTT assay values reflect an increase or decrease in the population of viable cells. To test for stimulation of the growth of chondrocytes, various test solutions containing PTH$_{1-34}$ were applied to the apical side of the chondrocyte monolayers, and the MTT assay was conducted at the beginning and then after 4 days incubation at 37° C./5% $CO_2$. The results showed that PTH$_{1-34}$ did not stimulate the growth of chondrocytes whether formulated as a simple solution or in the presence of permeation enhancers.

A cartilage growth model was examined, in which cells were provided in a form where they were encapsulated in alginate beads. In this form, human chondrocytes exhibit their phenotypic markers such as aggrecan and Type II collagen (Benya et al., 1982; Guo et al., 1982; Kato et al., 1984) unlike in monolayer culture where chondrocytes lose their phenotypic characteristics and de-differentiate to fibroblast-like cells (Kuettmer et al., 1982; Jennings et al., 1983; Kato et al., 1984). This alginate-based cell system was used to assess effect of $PTH_{1-34}$ dosing on Type II collagen expression as an indication of cartilage growth.

$PTH_{1-3}$ was tested for its ability to stimulate chondrocytes to produce cartilage. Cell-containing alginate beads were incubated in the presence of various test solutions for 12 days at 37° C., 5% $CO_2$. After the incubation, the alginate beads were processed using an extraction method in order to quantitate the production of Type II collagen (a major component of extracellular matrix of nasal cartilage (Shikani et al., 2004)).

Production of type II collagen was measured in positive (re-differentiation media) and negative (growth media) controls as well as the effect of exposing the cells to either 20 or 200 µg $PTH_{1-34}$. Low levels of type II collagen were produced in the presence of the re-differentiation media but not in the growth media. Application of 20 mg of $PTH_{1-34}$ did not cause production of type II collagen from the chondrocytes, either in citrate buffer or with permeation enhancers. When 200 mg of $PTH_{1-34}$ was applied to the cell culture in a simple formulation, the production of type II collagen was increased. Surprisingly, when the same amount of peptide was given in the formulation containing permeation enhancers, type II collagen was not produced by the cells. As a control, the cell system was validated in tests showing that production of type II collagen was increased by culturing with 5 mg IGF-I.

These results are consistent with a role of permeation enhancers such as methyl-b-cyclodextrin and/or DDPC in blocking the local activity of the $PTH_{1-34}$.

EXAMPLE 5

PK Study of $PTH_{1-34}$ in Rabbits

The objective of this study was to determine the plasma pharmacokinetics and relative intranasal and subcutaneous bioavailability of $PTH_{1-34}$ following intranasal or subcutaneous dose administration to rabbits. In addition, the absorption profile of subcutaneous recombinant and synthetic $PTH_{1-34}$ was evaluated.

This was a randomized, single treatment parallel study in four groups of four animals per group. Following dose administration, serial blood samples were obtained from each animal by direct venipuncture of a marginal ear vein. Serial blood samples (about 2 mL each) were collected by direct venipuncture from a marginal ear vein into blood collection tubes containing EDTA as the anticoagulant. After collection of the blood, the tubes were gently rocked several times immediately for anti-coagulation. Aprotinin at 100 µL was added to the collection tubes. Blood samples were collected at 0, 5, 10, 20, 30, 45, 60, 120 and 240 minutes post-dosing. Clinical observations were observed at least once daily and at all times of blood sampling.

Doses were based on the most recently recorded body weight. For intranasal and subcutaneous administration animals were dosed at the volume of 50 µL/kg and 5 µL/kg, respectively. The dose multiples were based on a nasal surface measurements of the rabbit and human. The nasal surface dose multiples of the rabbit compared to the human is approximately 2 fold in this study based on a unilateral nasal surface area of 30 $cm^2$ and 80 $cm^2$ for rabbit and humans, respectively. The dosing groups are presented in Table 4.

The nasal and subcutaneous formulations for Group 1, 2, 3 and 4 were according to the methods described above. An enzyme immunoassay was developed to measure the concentration of Human $PTH_{1-34}$ in rabbit serum. Samples were collected with protease inhibitor (aprotinin) and frozen. Samples, Standards, and Quality Control samples are assayed using a modified Human Bioactive $PTH_{1-34}$ ELISA kit. Standards, Samples, and Quality Control samples are added to streptavidin coated strip wells in duplicate. These samples are then incubated with a mixture of biotinylated human $PTH_{1-34}$ antibody and HRP-conjugated human $PTH_{1-34}$ antibody. The plate is washed with the kit Wash solution and TMB substrate solution is added to each well. Color is allowed to develop for 10 minutes before solution is added to each well. OD is measured on an absorbance plate reader. Concentration is calculated by interpolation of a standard curve and assay performance is controlled with Quality Control samples. Pharmacokinetic calculations were performed using WinNonLin software (Pharsight Corporation, Version 4.0, Mountain View, Calif.) using a non-compartmental model.

Group 1 and 2 were dosed at 50 µg/kg by the intranasal route using synthetic PTH from Bachem as the active ingredient. Group 1 was the marketed FORTLO® formulation and Group 2 was Nastech's formulation. Group 3 and 4 were dosed at 5 µg/kg by the subcutaneous route using recombinant and synthetic PTH, respectively. The excipients used for the subcutaneous route were the same as FORTLO® marketed product for both groups.

The mean $C_{max}$ was 1,921.13, 2,559.28, 1,538.10 and 2,526.43 pg/mL for Group 1, 2, 3 and 4, respectively. The mean $T_{max}$ was 35, 20, 20 and 10 minutes for group 1, 2, 3 and 4 respectively. The $C_{max}$ for group 2 was 1.3, 1.7 fold greater and approximately the same compared to groups 1, 3, and 4, respectively. However, the dose for group 2 was 10 fold higher than group 3 and 4. The relative bioavailability for Group 2 corrected for dose was 16.6 and 10.0% compared to groups 3 and 4 for $C_{max}$, respectively. The $C_{max}$ for Group 2 was 1.3 fold higher than Group 1. The relative bioavailability comparing the subcutaneous routes $C_{max}$ was 61% for group 3 versus group 4.

The mean $AUC_{last}$ was 111,850.81, 123,498.63, 173,992.88 and 194,895.25 min*pg/mL for group 1, 2, 3 and 4, respectively. The mean $AUC_{inf}$ was 118,022.48, 130,377.44, 177,755.35 and 206,317.05 for group 1, 2, 3 and 4 respectively. The relative bioavailability for Group 2 corrected for dose was 7.1 and 6.3% compared to groups 3 and 4 for $AUC_{last}$, respectively. The relative bioavailability for Group 2 corrected for dose was 7.3 and 6.3% compared to groups 3 and 4 for $AUC_{inf}$, respectively. The $AUC_{last}$ and infinity for Group 2 was 1.1 fold higher than Group 1. The relative bioavailability comparing the subcutaneous routes $AUC_{last}$ was 89.3% for group 3 versus group 4. The relative bioavailability comparing the subcutaneous routes $AUC_{inf}$ was 86.2% for group 3 versus group 4.

Based on the human pharmacokinetic data that tested the approved subcutaneous FORTLO® at a dose of 20 µg, the human dose systemic exposure multiple for Group 2 are approximately 20, 8.4 and 7.4 fold for $C_{max}$, $AUC_{last}$, and $ADC_{inf}$ respectively. The nasal exposure in the study is approximately 2 fold based on the mean rabbit weight of 2.5 kg and nasal surface area of 30 cm² and 80 cm² for rabbits and humans, respectively.

The $t_{1/2}$ of $PTH_{1-34}$ ranges from approximately 43-55 minutes for all groups. The mean $t_{max}$ was 35, 20, 20 and 10 minutes for groups 1, 2, 3 and 4, respectively. Kel was 0.018, 0.017, 0.016 and 0.014 for groups 1, 2, 3 and 4, respectively. No adverse clinical signs were observed following dosing of any formulation.

On a $C_{max}$ and AUC basis the relative bioavailability of formulation of the invention was approximately 10%. Other intranasal studies conducted in rabbits with $PYY_{3-36}$ as the active with a similar formulation matrix also had an approximate 19% bioavailability and when tested in humans resulted in a similar bioavailability. Therefore, human intranasal dose is 200 μg in contrast to to the FORTEO® subcutaneous dose of 20 μg.

Even though formulation of the invention had a higher $C_{max}$, AUC and a faster $T_{max}$, Group 1 had an unexpected high absorption rate as compared to Group 2, 3 and 4. consistent with in-vitro studies.

Synthetic $PTH_{1-34}$ has a higher absorption rate than the recombinant $PTH_{1-34}$ given by the subcutaneous route. The levels reached in this study with formulation of the invention are approximately 20 and 8.4 fold for $C_{max}$ and $AUC_{last}$ based on a human dose of 20 μg. Based on a nasal surface area basis, the doses tested in this study are approximately 2 fold. Therefore, the doses chosen in the 14 day toxicity studies of 50 and 250 μg give an appropriate comparison to the human dose for nasal and systemic exposure.

EXAMPLE 6

PK Study of $PTH_{1-34}$

This study was conducted to determine the pharmacokinetic profile of teriparatide (human parathyroid hormone 1-34 ($hPTH_{1-34}$)) in selected formulations following intranasal administration in the rabbit.

The overall study design is provided in Table 5. The dose level was selected based on previous studies with teriparatide dosed via intranasal instillation.

Each animal was dosed by intranasal instillation into the left nare. Blood samples were taken from the marginal ear vein, pre-dose and 5, 10, 20, 30, 45 minutes and 1 (60 minutes), 2 (120 minutes) and 4 hours (240 minutes) post-dose. Blood sampling and handling were conducted per protocol, with no deviations that were considered to impact sample quality. Blood samples were collected with a protease inhibitor (Aprotinin), processed for harvest of serum and plasma, and frozen and stored at −70° C. until analyzed.

Five nasal formulations of teriparatide were evaluated in the study. The vehicle composition for each formulation is provided in Table 6. The nasal formulations of the invention were manufactured at Nastech Pharmaceutical Company Inc. (Bothell, Wash.).

An enzyme immunoassay was developed (serum and plasma) and validated (serum) to measure the concentration of human $PTH_{1-34}$ in blood samples from rabbit. Study samples, Standards, and Quality Control samples were assayed using a modified Human Bioactive $PTH_{1-34}$ ELISA kit. Standards, Samples, and Quality Control samples were added to streptavidin coated strip wells, with each sample analyzed in duplicate. Samples were incubated with a mixture of biotinylated anti-human $PTH_{1-34}$ antibody and HRP-conjugated anti-human $PTH_{1-34}$ antibody. The plate was washed with the kit wash solution and TMB substrate solution was added to each well. Color was allowed to develop for 10 minutes before the reaction was stopped by the addition of 1 M sulfuric acid to each well. The $OD_{450}$ for each well was measured on an absorbance plate reader, and the concentration was calculated by interpolation from the standard curve. Assay performance was monitored with Quality Control samples. The assay Lower Limit of Quantification (LLOQ) was determined to be 7.8 pg/mL using human $PTH_{1-34}$ as the standard analyte and normal rabbit serum or plasma.

Due to species similarity between rabbit and human parathyroid hormones, it was anticipated the assay would detect endogenous (i.e., rabbit) parathyroid hormone and rabbit-$PTH_{1-34}$. Pharmacokinetic calculations as described above.

Pre-dose concentrations of PTH (assumed to represent rabbit parathyroid hormone or its fragments) in serum or plasma were generally below 100 pg/mL, with several samples determined to be <62.4 pg/mL. Limitations on sample volume precluded repeated analysis to obtain definitive results or the assay LLOQ. The value provided is the lowest value (or estimated value) obtained at which no further analysis was possible.

Individual animal serum and plasma values for teriparatide exceeded 100 pg/mL at the 5 through 60 minute time points. At the final time points, particularly 240 minutes, the majority of the animals had teriparatide concentrations of <31.2 pg/mL (the last point at which sample volume was insufficient for further evaluation). Thus the absorption and elimination phases for teriparatide were captured by the sampling time frame employed for the study.

Formulation 1/Group 1:

The $C_{max}$, $t_{1/2}$, and $AUC_{last}$ results for serum and plasma of the Group 1 animals greatly exceed the expected values based on dose level. Pre-dose values for each of the four animals in Group 1 were within the expected range, indicating the animals endogenous levels were not a factor in this observation. Animals #931 had teriparatide values in serum and plasma at the 5- and 10-minute that that were within the expected range. The 5-minute time point for Animal #932 was within the expected range, while at 10-minutes post-dose the assay value for plasma was >250,000 pg/mL. Subsequent time points for both animals were found to have concentrations of >30,000 pg/mL in serum or plasma. For Animals #933 and #934, all post-dose time points for serum and plasma were found to have teriparatide concentrations that were >30,000 pg/mL. As a result, $C_{max}$ was >45,000 pg/mL and the $t_{1/2}$ was >300 minutes for the majority of animals. Mean $AUC_{last}$ was >7,000,000 min*pg/mL.

The mean $T_{max}$ of 29 and 20 minutes for serum and plasma, respectively, were consistent with the expected range for intranasal dosing. However, the measured $C_{max}$ of 30,000 to almost 50,000 pg/mL were an order of magnitude high than the expected maximal concentrations of 3000 to 5000 pg/mL.

Formulation 2/Group 2:

In serum, the group mean $C_{max}$ and $T_{max}$ were 4396 pg/mL and 36 minutes, respectively. The group mean $t_{1/2}$ was 70.7 minutes, however, this was influenced by Animal #935 in which the calculated $t_{1/2}$ was 198 minutes; the $t_{1/2}$ for the other three animals was 37.7, 22.7, and 24.6 minutes. The mean $AUC_{last}$ was 307213 min*pg/mL. The mean $C_{max}$ and $AUC_{last}$ in plasma were 3819 pg/mL and 105144 min*pg/mL, respectively. $T_{max}$ was estimated to be 9 minutes and the $t_{1/2}$ was 66.9 minutes.

Formulation 3/Group 3:

$C_{max}$, $T_{max}$, $t_{1/2}$, and $AUC_{last}$ in serum were 1224 pg/mL, 9 minutes, 53 minutes, and 35111 min*pg/mL, respectively. In plasma, $C_{max}$, $T_{max}$, and $AUC_{last}$ were 1102 pg/mL, 8 minutes, and 53283 min*pg/mL, respectively. The mean $t_{1/2}$ was estimated to be 99.7 mutes, however, this was attributable to a long $t_{1/2}$ (216.6 minutes) for Animal #939.

Formulation 4/Group 4:

In serum, $C_{max}$, $T_{max}$, $t_{1/2}$, and $AUC_{last}$ were 653 pg/mL, 35 minutes, 22.3 minutes, and 30807 min*pg/mL, respectively. In plasma, these same parameters were 915 pg/mL, 35 minutes, 73.9 minutes, and 56383 min*pg/mL, respectively.

Formulation 5/Group 5:

In serum, $C_{max}$, $T_{max}$, $t_{1/2}$, and $AUC_{last}$ were 549 pg/mL, 45 minutes, 57.6 minutes, and 41489 min*pg/mL, respectively. In plasma, these same parameters in serum, and 734 pg/mL, 41 minutes, 48.8 minutes, and 23710.9 min*pg/1 nL, respectively.

The post-dose data for Group 1 demonstrate the unexpected high concentrations and absence of a clear elimination phase. This would be consistent with a contamination of a common solution in the collection procedure, and concentrations that are independent of dose administration.

For Groups 3 and 5 the mean concentration of teriparatide at each time point post-dose was similar between serum and plasma. The shape of the concentration vs. time curves was also similar between serum and plasma. In Group 2, peak concentrations of teriparatide were similar is serum and plasma, but serum was noted with higher concentrations at the latter time points. For Group 4, plasma concentrations of teriparatide were higher at the latter time points, as compared to serum; similar concentrations of were found in serum and plasma at the early time points after dosing. Overall, these results suggest that either plasma or serum may be an appropriate matrix for the determination of teriparatide concentrations after dose administration.

The data for Formulation 1/Group 1 was intended to be the set used for calculation of the comparative bioavailability for the other formulation, however, with consideration of the data obtained for this group any comparison was considered not to be appropriate. As an alternative, data from previous studies, above, were compiled to obtain a value for $C_{max}$ and $AUC_{last}$. Although the formulation components for these studies were slightly different, the primary components—methyl-β cyclodextrin, phosphatidylcholine didecanoyl, edetate disodium, and sodium benzoate—were present at similar concentrations to Formulation 1.

Using the compiled value for $C_{max}$ and $AUC_{last}$, the comparative bioavailability of teriparatide for each intranasal formulation/group was calculated. The $C_{max}$ and $AUC_{last}$ for Formulation 2/Group 2 were approximately equal to (serum) or slightly greater (plasma) than the compiled values, indicating comparable bioavailability. The primary difference for Formulation 2 was the concentration of phosphatidylcholine didecanoyl was decreased to 0.1 mg/mL (from 1.0 mg/mL).

Formulation 3 was dosed at half the dose volume, but contained 6.6 mg/mL teriparatide to achieve the same total dose. The concentration of methyl-β cyclodextrin, phosphatidylcholine didecanoyl, and edetate disodium were increased; sodium benzoate remained at the same concentration. The comparative bioavailability for Formulation 3 was approximately 40% for both serum and plasma.

Formulation 4 contains the components at the concentrations listed for FORTEO®, a subcutaneously delivered form of teriparatide.

Formulation 5 was this formulation with m-cresol removed. Relative bioavailability for Group 4 (Formulation 4) and Group 5 (Formulation 5) was approximately 30%-35% for serum or plasma. The data suggest that the presence of m-cresol did not have a significant impact of teriparatide bioavailability.

These results show that the concentration of phosphatidylcholine didecanoyl can be decreased from 1.0 mg/mL to 0.1 mg/mL without significantly decreasing bioavailability. Increasing the concentration of teriparatide and the absorption enhancers had an apparent negative impact upon the bioavailability. The cause for this drop may be related to reduction in surface area of contact with the nasal mucosa due to reduced volume. In the absence of absorption enhancers, the relative bioavailability was further decreased. This decreased bioavailability was expected due to the absence of any specific permeation enhancers, and is also consistent with in vitro permeation data. Subcutaneous injection is the route of administration most often used for nonclinical studies with teriparatide, and is the only route approved for clinical use. For Group 2, a relative bioavailability in the range of 5 to 17% is consistent previous estimate of 6-10%. Increasing the concentration of teriparatide and the absorption enhancers (Group 3) decreased the relative bioavailability to 2-5%. In the absence of absorption enhancers (groups 4 and 5) the relative bioavailability for teriparatide was approximately 2-3%.

EXAMPLE 7

PK Study of $PTH_{1-34}$ in Humans

The primary objectives of this study are to: evaluate the absorption of three formulations of the invention in a nasal spray at two dose levels; evaluate the safety of these formulations at two dose levels and to compare the bioavailability of Forsteo given subcutaneously with these formulations at two dose levels.

This is a phase I, crossover, dose ranging study involving 6 healthy male and 6 healthy female volunteers. There are five study periods as follows:

Period 1:

All 12 subjects receive Forsteo 20 µg subcutaneously.

Period 2:

6 (3 male and 3 female) subjects receive 500 µg of Formulation #2 and 6 (3 male and 3 female) subjects receive 500 µg of Formulation #3. The results of a total calcium level drawn four hours after dosing are used to determine the doses of these Formulations to be administered during Periods 4 and 5 as follows:

- If none of the six subjects who receive a given Formulation have a total calcium level≧3 mmol/L (12.0 mg/dL) at four hours post dose, then all doses of that Formulation in periods 4 or 5 are at 1000 µg.
- If a single subject of the six who receive a given Formulation has a total calcium level≧3 mmol/L (12.0 mg/dL) at four hours post dose, that subject receive only a 500 µg dose of Formulations 2 and 3 during Periods 4 and 5.
- If 2 or more subjects of the six who receive a given Formulation have a total calcium level≧3 mmol/L (12.0 mg/dL) at four hours post dose, all subjects receive a 500 µg dose of that Formulation during Periods 4 or 5.

Period 3:

All subjects receive 1000 µg of Formulation #1.

Period 4:

All subjects receive a dose of Formulation #2 at either 500 μg or 1000 μg as described above.

Period 5:

All subjects receive a dose of Formulation #3 at either 500 μg or 1000 μg as described above.

Subjects are confined to the study center from Day −1 until all study activities have been completed on Dosing Day #5. Safety assessments include vital signs, clinical laboratory evaluations, nasal tolerance and adverse events.

Blood samples for PK analysis of teriparatide levels are collected via an indwelling catheter and/or via direct venipuncture. These samples will be collected at 0 (i.e., pre-first-dose), 5, 10, 15, 30, 45, 60, 90 minutes and 2, 3, and 4 hours post-dose.

At each time point, 7 mL of blood will be collected. Plasma concentrations of teriparatide are determined using a validated analytical procedure.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation.

TABLE 1

PTH formulation composition

| Formulations | $PTH_{1-34}$ Per 100 ml Sample | Mucosal Delivery Enhancing Agent |
|---|---|---|
| A | 60 μg | Phosphate-buffered saline (0.8%) pH 7.4 (Control 1) |
| B | 60 μg | Phosphate-buffered saline (0.8%) pH 5.0 (Control 2) |
| C | 60 μg | L-Arginine (10% w/v) |
| D | 60 μg | Poly-L-Arginine (0.5% w/v) |
| E | 60 μg | Gamma-Cyclodextrin (1% w/v) |
| F | 60 μg | α-Cyclodextrin (5% w/v) |
| G | 60 μg | Methyl-β-Cyclodextrin (3% w/v) |
| H | 60 μg | n-Capric Acid Sodium (0.075% w/v) |
| I | 60 μg | Chitosan (0.5% w/v) |
| J | 60 μg | L-α-phosphatidilcholine didecanyl (3.5% w/v) |
| K | 60 μg | S-Nitroso-N-Acetyl-Penicillamine (0.5% w/v) |
| L | 60 μg | Palmotoyl-DL-Carnitine (0.02% w/v) |
| M | 60 μg | Pluronic-127 (0.3% w/v) |
| N | 60 μg | Sodium Nitroprusside (0.3% w/v) |
| O | 60 μg | Sodium Glycocholate (1% w/v) |
| P | 60 μg | F1: Gelatin, DDPC, MBCD, EDTA |
| F 1 | | L-α-phosphatidilcholine didecanyl (0.5% w/v) Methyl β Cyclodextrin (3% w/v) EDTA (0.1% w/v, Inf. Conc. 0.5 M) Gelatin (0.5% w/v) |

TABLE 2

| Ingredient Name | g/100 mL | Theoretical Weight (Grams) |
|---|---|---|
| $PTH_{1-34}$, GMP grade | 0.022 | 0.0066 |
| Chlorobutanol, NF (anhydrous) | 0.50 | 1.25 |
| Methyl-β-Cyclodextrin | 4.50 | 11.25 |
| L-α-Phosphatidylcholine Didecanoyl | 0.10 | 0.25 |
| Edetate Disodium, USP | 0.10 | 0.25 |
| Sodium Citrate dihydrate, USP | 0.1800 | 0.45 |
| Citric acid anhydrous, USP | 0.0745 | 0.1863 |
| Lactose monohydrate, NF | 0.90 | 2.25 |

TABLE 2-continued

| Ingredient Name | g/100 mL | Theoretical Weight (Grams) |
|---|---|---|
| Sorbitol, NF | 1.82 | 4.55 |
| Hydrochloric acid, NF | TAP* | TAP |
| Sodium Hydroxide, USP | TAP | TAP |
| Sterile Water for Irrigation, USP | 94.03 ** | 235.075 |

TABLE 3

Formula for PTH1–34 Nasal Spray solution

| Ingredient Name | g/100 mL | Theoretical Weight (Grams) |
|---|---|---|
| Chlorobutanol, NF (anhydrous) | 0.50 | 1.25 |
| Methyl-β-Cyclodextrin | 4.50 | 11.25 |
| L-α-Phosphatidylcholine Didecanoyl | 0.10 | 0.25 |
| Edetate Disodium, USP | 0.10 | 0.25 |
| Sodium Citrate dehydrate, USP | 0.18 | 0.45 |
| Citric acid anhydrous, USP | 0.0745 | 0.1863 |
| Lactose monohydrate, NF | 0.90 | 2.25 |
| Sorbitol, NF | 1.82 | 4.55 |
| Hydrochloric acid, NF | TAP | TAP |
| Sodium hydroxide, USP | TAP | TAP |
| Sterile Water for Irrigation, USP | 94.03* | 235.075 |

TAP = To adjust pH.
*= Using experimentally determined diluent density of 1.022 g/mL

TABLE 4

Dosing Groups for Toxicokinetic Animals

| Group | Animals | Route of Administration Formulation | Dose Conc (mg/mL) | Dose Vol (mL/kg) | Dose Level (μg/kg) |
|---|---|---|---|---|---|
| 1 | 4M | Intranasal (Bachem PTH Marketed Formulation) | 3.33 | 0.015 | 50 |
| 2 | 4M | Intranasal (Bachem PTH Nastech Formulation) | 3.33 | 0.015 | 50 |
| 3 | 4M | Subcutaneous (Sub-Q) (Marketed Product) | 0.025 | 0.2 | 5 |
| 4 | 4M | Subcutaneous (Sub-Q) (Bachem PTH Marketed Formulation) | 0.025 | 0.2 | 5 |

TABLE 5

Dosing Groups for Pharmacokinetic Evaluation

| Study Groups | Animals | Route of Administration (Formulation) | Teriparatide Concentration (mg/mL) | Dose Volume (mL/kg) | Teriparatide Dose Level (μg/kg) |
|---|---|---|---|---|---|
| 1 | 4M | Intranasal (Formulation 1) | 3.33 | 0.015 | 50 |
| 2 | 4M | Intranasal (Formulation 2) | 3.33 | 0.015 | 50 |
| 3 | 4M | Intranasal (Formulation 3) | 6.6 | 0.0075 | 50 |
| 4 | 4M | Intranasal (Formulation 4) | 3.33 | 0.015 | 50 |
| 5 | 4M | Intranasal (Formulation 5) | 3.33 | 0.015 | 50 |

TABLE 6

Vehicle Composition for Formulations 1–5

| Component | mg/mL (% w/w) |
|---|---|
| Formulation 1 | |
| Methyl-β Cyclodextrin | 45 (4.5) |
| Phosphatidylcholine didecanoyl (DDPC) | 1.0 (0.1) |
| Edetate Disodium, USP | 1.0 (0.1) |
| Sodium Benzoate, NF | 4.0 (0.4) |
| Sodium Hydroxide, USP | TAP |
| Hydrochloric Acid, NF | TAP |
| Sterile Water for Irrigation, USP | q.s |
| pH = 4.5 | |
| Formulation 2 | |
| Methyl-β Cyclodextrin | 45 (4.5) |
| Phosphatidylcholine didecanoyl (DDPC) | 0.1 (0.01) |
| Edetate Disodium, USP | 1.0 (0.1) |
| Sodium Benzoate, NF | 4.0 (0.4) |
| Sodium Hydroxide, USP | TAP |
| Hydrochloric Acid, NF | TAP |
| Sterile Water for Irrigation, USP | q.s |
| pH = 4.5 | |
| Formulation 3 | |
| Methyl-β Cyclodextrin | 90 (9.0) |
| Phosphatidylcholine didecanoyl (DDPC) | 2.0 (0.2) |
| Edetate Disodium, USP | 2.0 (0.2) |
| Sodium Benzoate, NF | 4.0 (0.4) |
| Sodium Hydroxide, USP | TAP |
| Hydrochloric Acid, NF | TAP |
| Sterile Water for Irrigation, USP | q.s |
| pH = 4.5 | |
| Formulation 4 | |
| Mannitol, USP | 30.8 (3.08) |
| M-Cresol | 3.0 (0.3) |
| Glacial Acetic Acid, USP | 0.42 (0.042) |
| Sodium Acetate, Anhydrous, USP | 0.1 (0.01) |
| Sodium Hydroxide, USP | TAP |
| Hydrochloric Acid, NF | TAP |
| Sterile Water for Irrigation, USP | q.s |
| pH = 4.0 | |
| Formulation 5 | |
| Mannitol, USP | 30.8 (3.08) |
| Glacial Acetic Acid, USP | 0.42 (0.042) |
| Sodium Acetate, Anhydrous, USP | 0.1 (0.01) |
| Sodium Hydroxide, USP | TAP |
| Hydrochloric Acid, NF | TAP |
| Sterile Water for Irrigation, USP | q.s |
| pH = 4.0 | |

TAP = added to adjust final pH

---

What is claimed is:

1. A formulation for delivery of PTH across a mucosal cellular layer, comprising an aqueous mixture of PTH, a cyclodextran and didecanoylphosphatidylcholine at concentrations sufficient to enhance permeation across the cellular layer, wherein the formulation consists of droplets, of which less than 10% are less than 10 microns in diameter.

2. The PTH formulation of claim 1, wherein said mixture further comprises a molecule capable of blocking the activity of PTH in chondrocytes.

3. The PTH formulation of claim 1, wherein the cyclodextran is selected from the group consisting of hydroxypropyl-β-cyclodextran, sulfobutylether-β-cyclodextran, and methyl-β-cyclodextrin.

4. The PTH formulation of claim 1 further comprising a chelating agent selected from the group consisting of ethylene diamine tetraacetic acid and ethylene glycol tetraacetic acid.

5. The PTH formulation of claim 1 further comprising one or more polyols.

6. The PTH formulation of claim 5, wherein the one or more polyols are selected from the group consisting of sucrose, mannitol, sorbitol, lactose, L-arabinose, D-erythrose, D-ribose, D-xylose, D-mannose, trehalose, D-galactose, lactulose, cellobiose, gentibiose, glycerin, and polyethylene glycol.

7. The PTH formulation of claim 6, wherein the one or more polyols are lactose and sorbitol.

8. The PTH formulation of claim 1 further comprising one or more surface-active agents.

9. The PTH formulation of claim 8, wherein the surface-active agent is selected from the group consisting of non-ionic polyoxyethylene ether, bile salts, sodium glycocholate, deoxycholate, fusidic acid and its derivatives, sodium taurodihydrofusidate, polysorbate 80, polysorbate 20, polyethylene glycol, cetyl alcohol, polyvinylpyrolidone, polyvinyl alcohol, lanolin alcohol, and sorbitan monooleate.

10. The PTH formulation of claim 1, wherein the mixture further comprises water and a preservative selected from the group consisting of chlorobutanol, methyl paraben, propyl paraben, butyl paraben, benzalkonium chloride, benzethonium chloride, sodium benzoate, sorbic acid, phenol, ortho-, meta-, and paracresol.

11. The PTH formulation of claim 10, wherein the formulation has a pH of about 3 to about 6.

12. The PTH formulation of claim 1, wherein the PTH molecule is selected from the group consisting of SEQ NO: 1, SEQ NO: 2, and SEQ NO: 3.

13. The formulation of claim 1, wherein the cyclodextran is methyl-β-cycodextran.

14. A method of delivering PTH to a human, comprising exposing a layer of mucosal cells to an aqueous mixture of PTH, a cyclodextran, and didecanoylphosphatidylcholine at concentrations sufficient to enhance permeation across the cellular layer, the mixture consisting of droplets, of which less than 10% are less than 10 microns in diameter.

15. The method of delivering PTH of claim 14, wherein said method utilizes a non-parenteral administration.

16. The method of delivering PTH of claim 15, wherein said method of administration is selected from the group consisting of intranasal, buccal, gastrointestinal, vaginal and transdermal.

17. The method of delivering PTH of claim 16, wherein said method is an intranasal administration.

18. The method of delivering PTH of claim 17, wherein said intranasal administration comprises delivering an aerosol comprising droplets of between 1 and 700 microns in size.

19. The method of delivering PTH of claim 17, wherein said intranasal administration comprises delivering an aerosol comprising about 0.7 to about 25 μg PTH per kg weight of the patient.

20. The method of delivering PTH of claim 19, wherein said intranasal administration comprises delivering an aerosol comprising 50 to 800 μg PTH.

21. The method of delivering PTH of claim 15, wherein said method is an oral delivery.

22. The method of delivering PTH of claim 21, wherein said oral delivery is a controlled release delivery wherein Tmax is less than 40 minutes from the time of release.

23. A method of treating osteoporosis or osteopenia in a human comprising administering an aqueous mixture of PTH, a cyclodextran, and didecanoylphosphatidylcholin at concentrations sufficient to enhance permeation across the cellular layer, wherein the mixture consisting of droplets, of which less than 10% are less than 10 microns in diameter.

24. The method of treating osteoporosis or osteopenia of claim 23, wherein said method of administration is selected from the group consisting of intranasal, buccal, gastrointestinal, vaginal and transdermal.

25. The method of treating osteoporosis or osteopenia of claim 23, wherein said administration causes a PTH serum level having a Tmax less than 40 minutes.

26. The method of treating osteoporosis or osteopenia of claim 23, wherein said administration causes a PTH serum level above background for less than four hours.

27. The method of treating osteoporosis or osteopenia of claim 23, wherein said administration is intranasal.

28. The method of treating osteoporosis or osteopenia of claim 27, wherein said intranasal administration comprises delivering an aerosol comprising about 0.3 to about 30 µg PTH per kg weight of the patient.

29. The method of treating osteoporosis or osteopenia of claim 27, wherein said intranasal administration comprises delivering an aerosol comprising 0.5 to 1.0 mg PTH per 0.1 ml of solution.

30. The method of treating osteoporosis or osteopenia of claim 29, wherein said intranasal administration is given at a dosage frequency of between 0.1 to 24 hours.

31. The method of treating osteoporosis or osteopenia of claim 29, wherein said intranasal administration comprises the following steps:

a. fill a nasal spray pump unit with a PTH solution;

b. prime the spray unit;

c. remove spray droplets present outside the spray unit;

d. tilt until the spray unit is in a straight line with a nasal passage; and e. spray the solution into the nasal passage.

32. An aqueous formulation for the delivery of PTH across a mucosal cellular layer, consisting of PTH, a cyclodextran, didecanoylphosphatidylcholine, chlorobutanol, sorbitol, and water at concentrations sufficient to enhance permeation across the cellular layer, the formulation consisting of droplets, of which less than 10% are less than 10 microns in diameter.

* * * * *

UNITED STATES PATENT AND TRADEMARK OFFICE
CERTIFICATE OF CORRECTION

PATENT NO. : 7,244,709 B2
APPLICATION NO. : 11/126996
DATED : July 17, 2007
INVENTOR(S) : S.C. Quay et al.

It is certified that error appears in the above-identified patent and that said Letters Patent is hereby corrected as shown below:

| COLUMN | LINE | ERROR |
| --- | --- | --- |
| (75) Pg. 1, col. 1 | Inventors | "Kingston," should read --Snohomish,-- |
| (73) Pg. 1, col. 1 | Assignee | "Pharamecutical" should read --Pharmaceutical-- |
| (56) Pg. 1, col. 2 | Refs. Cited (Foreign Pats., Item 5) | "WO 2005051456" should read --WO 05051456-- |
| (56) Pg. 1, col. 2 | Refs. Cited (Foreign Pats., Item 6) | "WO 2005115441" should read --WO 05115441-- |
| 1 | 31 | "df" should read --of-- |
| 1 | 47 | "cells both" should read --cells, both-- |
| 2 | 18, 19 | "280:6228; (1980)" should read --280:6228 (1980);-- |
| 2 | 30 | "postnenopausal" should read --postmenopausal-- |
| 2 | 58 | "been previously been" should read --been previously-- |
| 3 | 12 | "peptide, is" should read --peptide is-- |
| 3 | 56 | "Gin" should read --Gln-- |
| 3 | 66 | "actuator form" should read --actuator to form-- |
| 3 | 67 | "1-2," should read --1-2;-- |
| 4 | 57 | "referably" should read --preferably-- |
| 4 | 61 | "invention is" should read --invention-- |
| 5 | 49 | "formulation contain" should read --formulation contained-- |

UNITED STATES PATENT AND TRADEMARK OFFICE
CERTIFICATE OF CORRECTION

PATENT NO. : 7,244,709 B2
APPLICATION NO. : 11/126996
DATED : July 17, 2007
INVENTOR(S) : S.C. Quay et al.

It is certified that error appears in the above-identified patent and that said Letters Patent is hereby corrected as shown below:

| COLUMN | LINE | ERROR (continued) |
|---|---|---|
| 5 | 62 | "attached an" should read --attached to an-- |
| 6 | 31 | "includes PTH" should read --includes the PTH-- |
| 7 | 53 | "molecule (viii)" should read --molecule, (viii)-- |
| 7 | 56 | "acid (xi)" should read --acid, (xi)-- |
| 8 | 1 | "peptides (s)" should read --peptide(s)-- |
| 8 | 22 | "when at 50" should read --when 50-- |
| 9 | 9 | "intestional," should read --intestinal,-- |
| 9 | 29 | "reducing increasing" should read --increasing-- |
| 9 | 30 | "resporption" should read --resorption-- |
| 10 | 18 | "ries, can" should read --ries can-- |
| 10 | 61 | "properties the" should read --properties of the-- |
| 13 | 25 | "lysine etc--" should read --lysine, etc.-- |
| 13 | 37 | delete "polyoxyethylene alkyl esters," |
| 16 | 10 | "additives are" should read --additives is-- |
| 16 | 30 | "are available" should read --is available-- |
| 17 | 38 | "agents are" should read --agents is-- |
| 18 | 10 | "glycosidases which allow" should read --glycosidases allow-- |
| 18 | 34 | "delivery these" should read --delivery of these-- |
| 19 | 12 | "molecule (viii)" should read --molecule, (viii)-- |

UNITED STATES PATENT AND TRADEMARK OFFICE
CERTIFICATE OF CORRECTION

PATENT NO.       : 7,244,709 B2
APPLICATION NO.  : 11/126996
DATED            : July 17, 2007
INVENTOR(S)      : S.C. Quay et al.

It is certified that error appears in the above-identified patent and that said Letters Patent is hereby corrected as shown below:

| COLUMN | LINE | ERROR (continued) |
|---|---|---|
| 19 | 15 | "acid (xi)" should read --acid, (xi)-- |
| 19 | 30 | "Surfactants, which generally fall" should read --Surfactants generally fall-- |
| 19 | 53 | "provides pharmaceutical" should read --provides a --pharmaceutical-- |
| 21 | 61 | "diphtheria" should read --diphtheria-- |
| 22 | 25-26 | "agent (s)." should read --agent(s).-- |
| 23 | 38 | "then be" should read --then-- |
| 23 | 56-57 | "agent (s)." should read --agent(s).-- |
| 27 | 42 | "glue'," should read --glue';-- |
| 27 | 62 | "methods are" should read --methods is-- |
| 28 | 21 | "methods are" should read --methods is-- |
| 28 | 64 | delete "linoleic acid," |
| 28 | 67 | "C 12)" should read --C12)-- |
| 31 | 11 | "the power" should read --the powder-- |
| 32 | 33 | "weight compound" should read --weight compounds-- |
| 32 | 41 | "etc.)" should read --etc.).-- |
| 33 | 17 | "agent is" should read --agent are-- |
| 33 | 48 | "poly(E-aprolactone-" should read --poly(ε-aprolactone- -- |

UNITED STATES PATENT AND TRADEMARK OFFICE
CERTIFICATE OF CORRECTION

PATENT NO. : 7,244,709 B2
APPLICATION NO. : 11/126996
DATED : July 17, 2007
INVENTOR(S) : S.C. Quay et al.

It is certified that error appears in the above-identified patent and that said Letters Patent is hereby corrected as shown below:

| COLUMN | LINE | ERROR (continued) |
|---|---|---|
| 33 | 58 | "compositions e.g.," should read --compositions; e.g.,-- |
| 34 | 53 | "etc)," should read --etc.),-- |
| 36 | 7 | "the," should read --the-- |
| 36 | 13 | "administered in as" should read --administered as-- |
| 36 | 37 | "spray; it" should read --spray; it is-- |
| 36 | 41 | "drugproducts" should read --drug products-- |
| 36 | 50 | "course" should read --coarse-- |
| 37 | 35 | "distribution, The" should read --distribution. The-- |
| 37 | 59 | "nausa A" should read --nausea. A-- |
| 37 | 65 | "The a PTH" should read --The PTH-- |
| 40 | 60 | "burst" should read --burst.-- |
| 40 | 61 | "formation" should read --Formation-- |
| 42 | 38 | "medium as" should read --medium. As-- |
| 43 | 36 | "samples is" should read --samples are-- |
| 44 | 25 | "modified:" should read --modified.-- |
| 45 | 18 | after "below." indent and begin a new paragraph |
| 45 | 31 | "adjuste" should read --adjusted-- |
| 46 | 16 | "plated" should read --plates-- |
| 46 | 32 | "H" should read --II-- |

UNITED STATES PATENT AND TRADEMARK OFFICE
CERTIFICATE OF CORRECTION

PATENT NO. : 7,244,709 B2
APPLICATION NO. : 11/126996
DATED : July 17, 2007
INVENTOR(S) : S.C. Quay et al.

It is certified that error appears in the above-identified patent and that said Letters Patent is hereby corrected as shown below:

| COLUMN | LINE | ERROR (continued) |
|---|---|---|
| 46 | 48 | "days on" should read --days or-- |
| 46 | 52 | "Redmond Wash.)." should read --Redmond, Wash.).-- |
| 47 | 12 | "$PTH_{1-3}$" should read --$PTH_{1-34}$-- |
| 47 | 37 | "methyl-b-" should read --methyl-β- -- |
| 47 | 66 | "on a nasal" should read --on nasal-- |
| 48 | 31 | "FORTLO®" should read --FORTEO®-- |
| 48 | 36 | "FORTLO®" should read --FORTEO®-- |
| 48 | 64 | "FORTLO®" should read --FORTEO®-- |
| 49 | 20 | "4." should read --4,-- |
| 49 | 44 | "nare." should read --ear.-- |
| 50 | 14 | "calculations as" should read --calculations were as-- |
| 50 | 38 | "animals endogenous" should read --animals' endogenous-- |
| 50 | 39 | "Animals #931" should read --Animal #931-- |
| 50 | 56 | "high than" should read --higher than-- |
| 50 | 61 | "minutes, however," should read --minutes; however,-- |
| 51 | 6 | "mutes," should read --minutes,-- |
| 51 | 17 | "parameters in serum," should read --parameters; in serum;-- |
| 51 | 18 | "nL," should read --mL,-- |

UNITED STATES PATENT AND TRADEMARK OFFICE
CERTIFICATE OF CORRECTION

PATENT NO. : 7,244,709 B2
APPLICATION NO. : 11/126996
DATED : July 17, 2007
INVENTOR(S) : S.C. Quay et al.

It is certified that error appears in the above-identified patent and that said Letters Patent is hereby corrected as shown below:

| COLUMN | LINE | ERROR (continued) |
|---|---|---|
| 51 | 29 | "is serum" should read --in serum-- |
| 51 | 31 | "latter" should read --later-- |
| 51 | 32 | "latter" should read --later-- |
| 51 | 33 | "concentrations of were" should read --concentrations were-- |
| 51 | 40 | "formulation," should read --formulation;-- |
| 52 | 5 | "impact of" should read --impact on-- |
| 52 | 22 | "consistent previous" should read --consistent with previous-- |
| 52 | 58 | "subject receive" should read --subject receives-- |
| 57 (Claim 2, | 38-39 lines 2-3) | "actiy-ity" should read --activ-ity-- |

Signed and Sealed this

Twenty-ninth Day of January, 2008

JON W. DUDAS
*Director of the United States Patent and Trademark Office*